United States Patent [19]

Bartmann et al.

[11] Patent Number: 5,422,035
[45] Date of Patent: Jun. 6, 1995

[54] BENZENE DERIVATIVES, AND LIQUID-CRYSTALLINE MEDIUM

[75] Inventors: Ekkehard Bartmann, Erzhausen; Herbert Plach, Darmstadt; Andreas Ruhl, Rossdorf, all of Germany

[73] Assignee: Merck Patent Gesellschaft mit beschrankter Haftung, Darmstadt, Germany

[21] Appl. No.: 239,830

[22] Filed: May 9, 1994

[30] Foreign Application Priority Data

May 10, 1993 [DE] Germany .................. 43 15 371.2
Nov. 9, 1993 [DE] Germany .................. 43 38 164.2

[51] Int. Cl.⁶ .................. C09K 19/52; C07C 25/13; C07C 43/02
[52] U.S. Cl. .................. 252/299.01; 252/299.61; 252/299.63; 252/299.64; 252/299.65; 252/299.66; 570/127; 568/645; 568/656
[58] Field of Search .................. 252/299.01, 299.61, 252/299.62, 299.63, 299.64, 299.65; 568/656, 647, 634, 645; 570/127

[56] References Cited

U.S. PATENT DOCUMENTS 5,087,764  2/1992  Reiffenrath et al. .................. 568/656

FOREIGN PATENT DOCUMENTS 9001056  2/1990  WIPO .

*Primary Examiner*—Shean Wu
*Attorney, Agent, or Firm*—Millen, White, Zelano, & Branigan

[57] ABSTRACT

A liquid-crystalline medium based on a mixture of polar compounds having positive dielectric anisotropy, comprising one or more compounds of the formula I

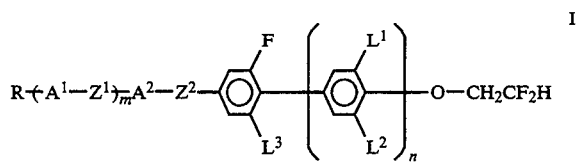

in which R, $A^1$, $A^2$, $Z^1$, $Z^2$, m, n, $L^1$, $L^2$ and $L^3$ are as defined in claim 1.

19 Claims, No Drawings

BENZENE DERIVATIVES, AND LIQUID-CRYSTALLINE MEDIUM

SUMMARY OF THE INVENTION

The present invention relates to benzene derivatives and to a liquid-crystalline medium, to the use of the latter for electrooptical purposes, and to displays containing this medium.

BACKGROUND OF THE INVENTION

Liquid crystals are used, in particular, as dielectrics in display devices since the optical properties of such substances can be effected by an applied voltage. Electrooptical devices based on liquid crystals are extremely well known to those skilled in the art and may be based on various effects. Devices of this type are, for example, cells having dynamic scattering, DAP (deformation of aligned phases) cells, guest/host cells, TN cells having a twisted nematic structure, STN (supertwisted nematic) cells, SBE (super-birefringence effect) cells and OMI (optical mode interference) cells. The most common display devices are based on the Schadt-Helfrich effect and have a twisted nematic structure.

The liquid-crystal materials must have good chemical and thermal stability and good stability toward electrical fields and electromagnetic radiation. Furthermore, the liquid-crystal materials should have low viscosity and give short addressing times, low threshold voltages and high contrast in the cells. Furthermore, they should have a suitable mesophase, for example, for the above-mentioned cells, a nematic or cholesteric mesophase, at customary operating temperatures, i.e. in the broadest possible range above and below room temperature. Since liquid crystals are generally used as mixtures of a plurality of components, it is important that the components are readily miscible with one another. Further properties, such as electrical conductivity, dielectric anisotropy and optical anisotropy, must meet various requirements depending on the cell type and the area of application. For example, materials for cells having a twisted nematic structure should have positive dielectric anisotropy and low electrical conductivity.

For example, the media desired for matrix liquid-crystal displays containing integrated nonlinear elements for switching individual image points (MLC displays) are those having high positive dielectric anisotropy, broad nematic phases, relatively low birefringence, very high specific resistance, good UV and temperature stability of the resistance and a low vapor pressure.

Matrix liquid-crystal displays of this type are known. Examples of nonlinear elements which can be used to individually switch the individual image points are active elements (i.e. transistors). This is then referred to as an "active matrix", and a differentiation can be made between two types:

1. MOS (Metal Oxide Semiconductor) or other diodes on a silicon wafer as substrate.
2. Thin-film transistors (TFTs) on a glass plate as substrate.

The use of monocrystalline silicon as the substrate material limits the display size since even the modular assembly of the various part displays results in problems at the joints.

In the case of the more promising type 2, which is preferred, the electrooptical effect used is usually the TN effect. A differentiation is made between two technologies: TFTs comprising compound semiconductors, such as, for example, CdSe, or TFTs based on polycrystalline or amorphous silicon. Intensive research efforts are being made worldwide in the latter technology.

The TFT matrix is applied to the inside of one glass plate of the display, while the inside of the other glass plate carries the transparent counterelectrode. Compared with the size of the image point electrode, the TFT is very small and hardly affects the image at all. This technology can also be extended to fully color-compatible image displays, where a mosaic of red, green and blue filters is arranged in such a manner that each filter element is located opposite a switchable image element.

The TFT displays usually operate as TN cells with crossed polarizers in transmission and are illuminated from the back.

The term MLC display here covers any matrix display containing integrated nonlinear elements, i.e. in addition to the active matrix, also displays containing passive elements such as varistors or diodes (MIM = metal-insulator-metal).

MLC displays of this type are particularly suitable for TV applications (for example pocket TV sets) or for high-information displays for computer applications (laptops) and in automobile or aircraft construction. In addition to problems with respect to the angle dependency of the contrast and the switching times, problems result in MLC displays due to inadequate specific resistance of the liquid-crystal mixtures TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288, Matrix LCD Controlled by Double Stage Diode Rings, p. 141 ff., Paris; STROMER, M., Proc. Eurodisplay 84, September 1984: Design of Thin Film Transistors for Matrix Addressing of Television Liquid Crystal Displays, p. 145 ff., Paris. As the resistance decreases, the contrast of an MLC display worsens and the problem of "afterimage elimination" may occur. Since the specific resistance of the liquid-crystal mixture generally decreases over the life of an MLC display due to interactions with the internal surfaces of the display, a high (initial) resistance is very important to give acceptable service lives. In particular in the case of low-voltage mixtures, it was hitherto not possible to achieve very high specific resistances. It is furthermore important that the specific resistance increases as little as possible with increasing temperature and after heating and/or exposure to UV radiation. The low-temperature properties of the mixtures from the prior art are also particularly disadvantageous. It is required that crystallization and/or smectic phases do not occur, even at low temperatures, and that the temperature dependence of the viscosity is as low as possible. The MLC displays of the prior art thus do not satisfy current demands.

Thus, there continues to be a great demand for MLC displays of very high specific resistance and at the same time a broad operating temperature range, short switching times, even at low temperatures and low threshold voltage which do not have these disadvantages or only do so to a lesser extent.

For TN (Schadt-Helfrich) cells, media are desired which facilitate the following advantages in the cells:
   broadened nematic phase range (in particular down to low temperatures), switchability at extremely low temperatures (outdoor use, automobiles, avionics), increased stability to UV radiation (longer life).

The media available from the prior art do not make it possible to achieve these advantages whilst simultaneously retaining the other parameters.

For supertwisted (STN) cells, media are desired which have a greater multiplexing ability and/or lower threshold voltages and/or broader nematic phase ranges (in particular at low temperatures). To this end, a further extension of the parameter latitude available (clearing point, smectic-nematic transition or melting point, viscosity, dielectric values, elastic values) is urgently desired.

SUMMARY OF THE INVENTION

The invention has an object of providing media, in particular for MLC, TN or STN displays of this type, which do not have the above-mentioned disadvantages or only do so to a lesser extent, and preferably at the same time have very high specific resistances and low threshold voltages.

It has now been found that this object can be achieved if media according to the invention are used in displays.

Upon further study of the specification and appended claims, further objects and advantages of this invention will become apparent to those skilled in the art.

The invention thus relates to a liquid-crystal-line medium based on a mixture of polar compounds having positive dielectric anisotropy, characterized in that it contains one or more compounds of the general formula I

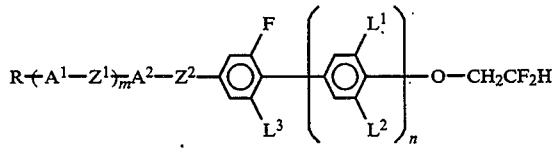

in which
R is H, an alkyl or alkenyl radical having 1 to 15 carbon atoms which is unsubstituted, monosubstituted by CN or $CF_3$ or mono- to perhalo-substituted by halogen(s), it also being possible for one or more $CH_2$ groups in these radicals to be replaced, in each case independently of one another, by —O—, —S—,

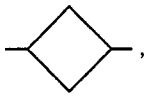

—CO—, —CO—O—, —O—CO— or —O—CO—O—, in such a way that O atoms are not linked directly to one another $A^1$ and $A^2$ are each, independently of one another, a
(a) trans-1,4-cyclohexylene radical in which, in addition, one or more non-adjacent $CH_2$ groups may be replaced by —O— and/or —S—,
(b) 1,4-phenylene radical in which, in addition, one or two CH groups may be replaced by N, or
(c) radical from the group consisting of 1,4-cyclohexenylene, 1,4-bicyclo(2,2,2)-octylene, piperidine-1,4-diyl, naphthalene-2,6-diyl, decahydronaphthalene-2,6-diyl and 1,2,3,4-tetrahydronaphthalene-2,6-diyl, it being possible for the radicals (a) and (b) to be substituted by one or two fluorine atoms, $Z^1$ and $Z^2$ are each, independently of one another, —CO—O—, —O—CO—, —$CH_2$O—, —O$CH_2$—, —$CH_2CH_2$—, —CH=CH—, —C≡C— or a single bond, and one of the radicals $Z^1$ and $Z^2$ is alternatively —$(CH_2)_4$— or —CH=CH—$CH_2CH_2$—, $L^1$, $L^2$ and $L^3$ are each, independently of one another, H or F, m is 0, 1 or 2, n is 0 or 1.

The compounds of the formula I have a broad range of application. Depending on the choice of substituents, these compounds can be used as the base materials from which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electro-optical use. They are stable, chemically, thermally and to light.

The invention also relates to the compounds of the formula I.

Compounds similar to formula I are included in the general formula in WO 90-01056. However, the specific fluorinated compounds according to the invention are not mentioned therein. The introduction of one or more fluorine atoms has a very considerable effect on the viscosity of the compounds.

Particular preference is given to compounds the formula I in which $L^3$ is F and n=0 or $L^3$=F and n=1. Preference is also given to compounds of the formula I and all sub-formulae in which $A^1$ is 1,4-phenylene which is monosubstituted or disubstituted by F or monosubstituted by CN. These are in particular wherein $A^1$ is fluoro-1,4-phenylene, 3-fluoro-1,4-phenylene, 3,5-difluoro-1,4-phenylene, 2-cyano-1,4-phenylene and 3-cyano-1,4-phenylene.

$Z^1$ and $Z^2$ are preferably a single bond or —$CH_2CH_2$—, and secondarily preferably —$CH_2$O—, —O$CH_2$—, —O—CO— or —CO—O—.

If one of the radicals $Z^1$ and $Z^2$ is —$(CH_2)_4$— or —CH=CH—$CH_2CH_2$—, the other radical $Z^1$ or $Z^2$ (if present) is preferably the single bond.

If R is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3, 4-, 5-, 6-, 7-, 8- or 9-oxadecyl.

If R is an alkyl radical which one $CH_2$ group has been replaced by $-CH=CH-$, this may be straight-chain or branched. It is preferably straight-chain and has 2 to 10 carbon atoms. It is accordingly in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one $CH_2$ group has been replaced by $-O-$ and one has been replaced by $-CO-$, these are preferably adjacent. These thus contain an acyloxy group $-CO-O-$ or an oxycarbonyl group $-O-CO-$. These are preferably straight-chain and have 2 to 6 carbon atoms.

They are accordingly in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbnyl)propyl, 3-(ethoxycarbonyl)propyl or 4-(methoxycarbonyl)butyl.

If R is an alkyl radical in which one $CH_2$ group has been replaced by unsubstituted or substituted $-CH=CH-$ and an adjacent $CH_2$ group has been replaced by CO or $CO-O$ or $O-CO$, this may be straight-chain or branched. It is preferably straight-chain and has 4 to 13 carbon atoms. It is accordingly in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R is an alkyl or alkenyl radical which is monosubstituted by CN or $CF_3$, this radical is preferably straight-chain. The substitution by CN or $CF_3$ is in any desired position.

If R is an alkyl or alkenyl radical which is at least monosubstituted by halogen, this radical is preferably straight-chain and halogen is preferably F or Cl. In the case of multiple substitution, halogen is preferably F. The resulting radicals also include perfluorinated radicals. In the case of monosubstitution, the fluorine or chlorine substituent may be in any desired position, but is preferably in the $\omega$-position.

Compounds of the formula I which contain wing groups R which are suitable for polymerization reactions are suitable for the preparation of liquid-crystalline polymers.

Compounds of the formula I containing branched wing groups R may occasionally be of importance due to better solubility in the customary liquid-crystalline base materials, but in particular as chiral dopes if they are optically active. Smectic compounds of this type are suitable as components of ferroelectric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If R is an alkyl radical in which two or more $CH_2$ groups have been replaced by $-O-$ and/or $-CO-O-$, this may be straight-chain or branched. It is preferably branched and has 3 to 12 carbon atoms. It is accordingly in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)hexyl.

Preferred smaller groups of compounds of the formula I are those of the subformulae I1 to I27:

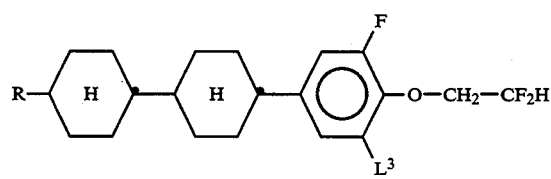

I1

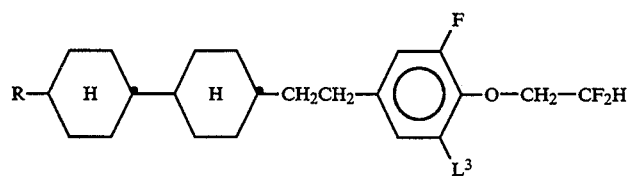

I2

-continued
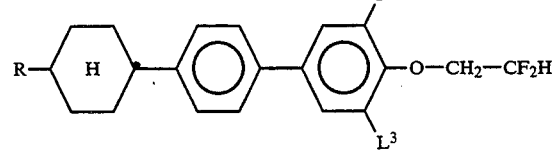
I3
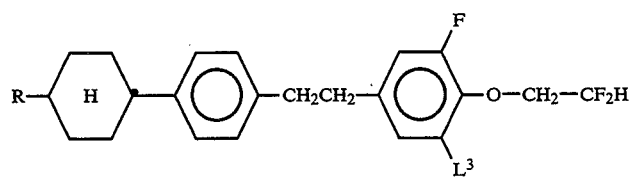
I4
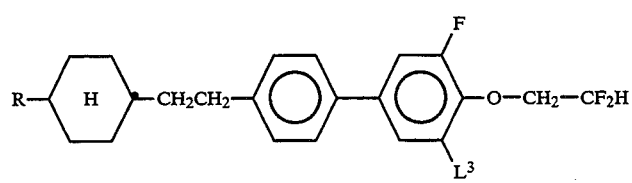
I5
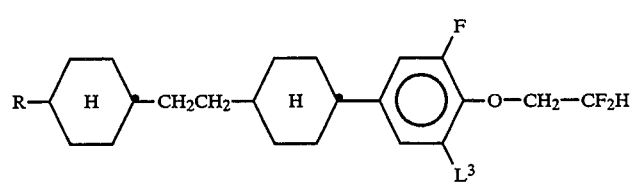
I6
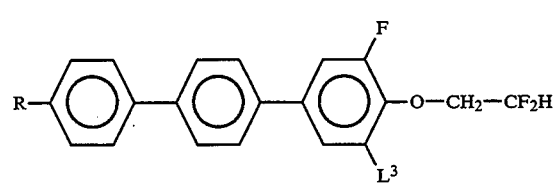
I7
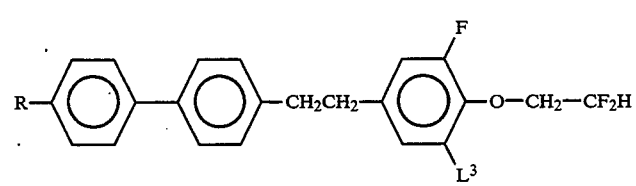
I8
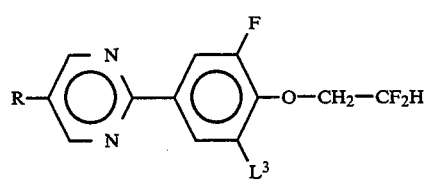
I9
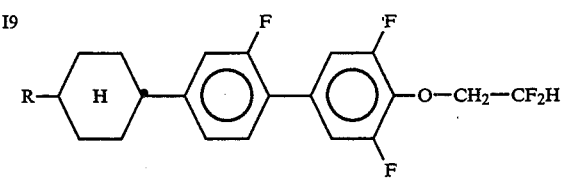
I10
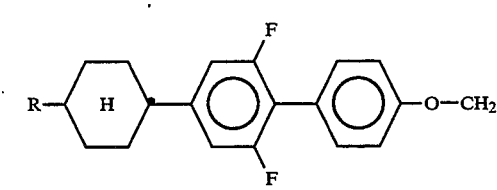
I11
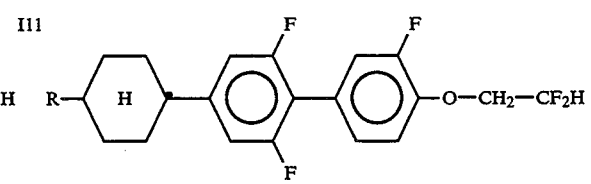
I12
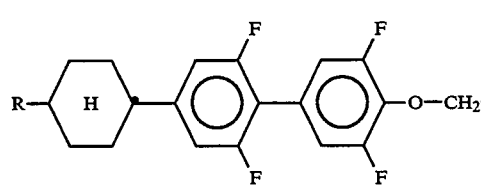
I13
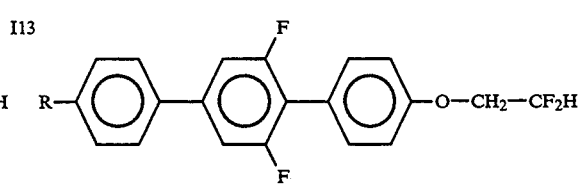
I14

-continued
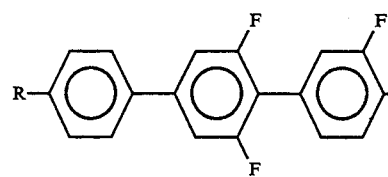     I15
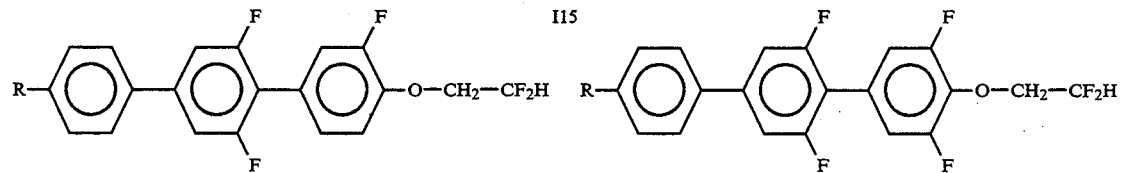     I16
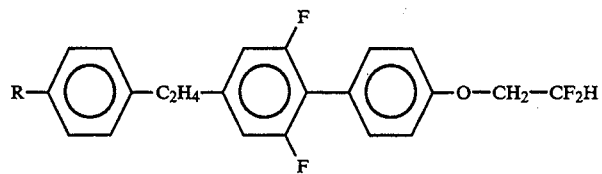     I17
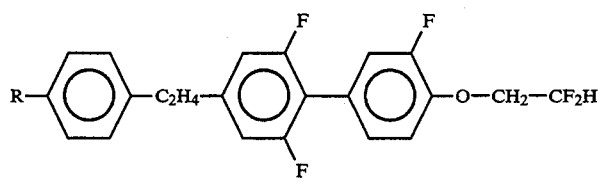     I18
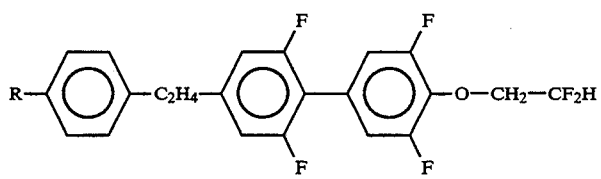     I19
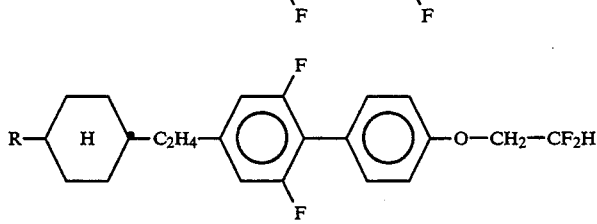     I20
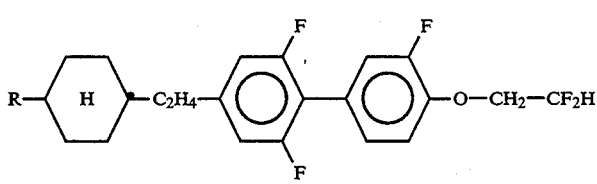     I21
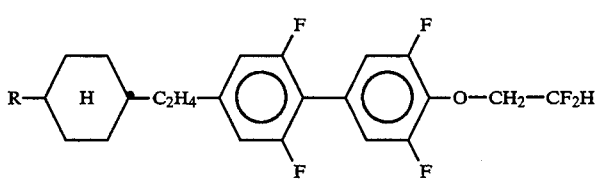     I22
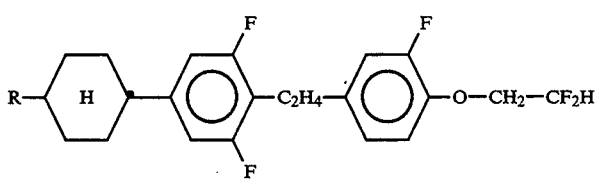     I23
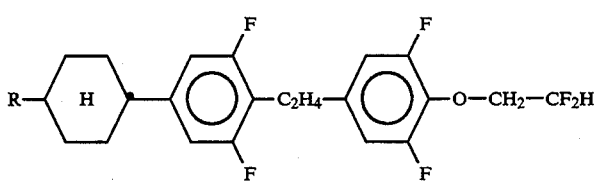     I24

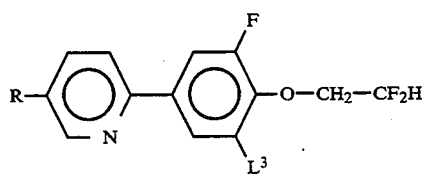 I25

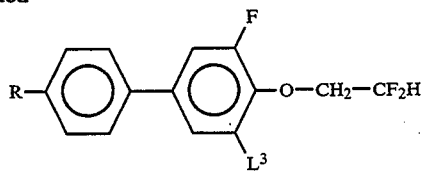 I26

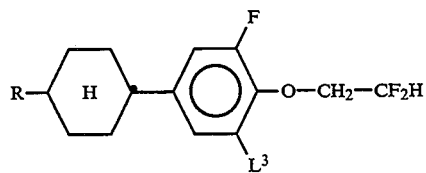 I27

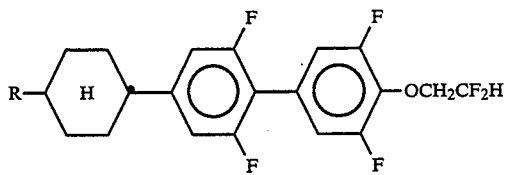 I28

Particular preference is given to compounds of the formulae I1, I3, I7, I10, I12, I13, I15, I16, I18, I19, I22, I23 and I24.

The 1,4-cyclohexenylene group preferably has the following structures:

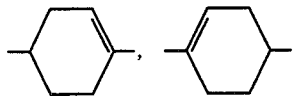

The compounds of the formula I are prepared by methods known per, as described in the literature (for example in the standard works, such as Houben-Weyl, Methoden der Organischen Chemie, Georg-Thieme-Verlag Stuttgart), to be precise under reaction conditions which are known and suitable for said reactions.

Use may also be made here of variants which are known per se, but are not described here in greater detail.

The compounds according to the invention can be prepared, for example, by metallating a compound of formula II,

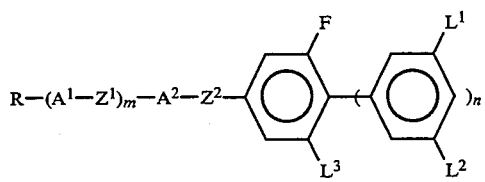 II in which R, $A^1$, $A^2$, $Z^1$, $Z^2$, $L^1$, $L^2$, $L^3$, m and n are as defined above, in accordance with the reaction scheme below, and subsequently reacting the product with a suitable electrophile:

Scheme 1

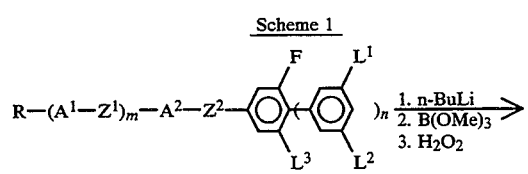

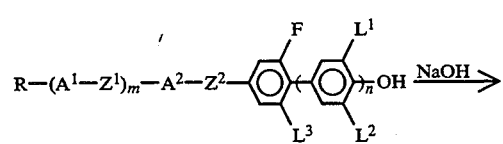

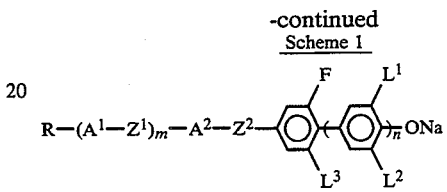

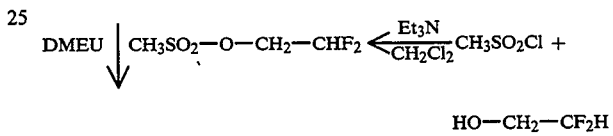

Scheme 2

($L^{1-4}$: H or F; R* = halogen, formyl)

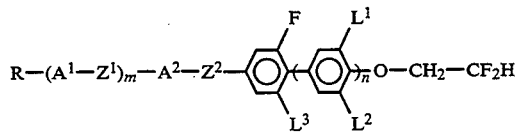

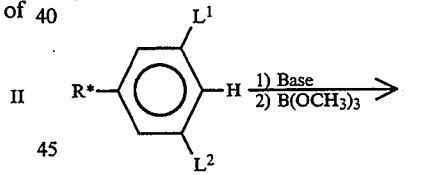

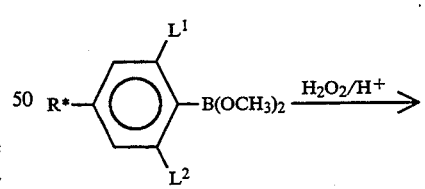

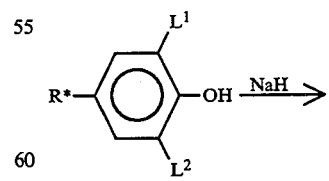

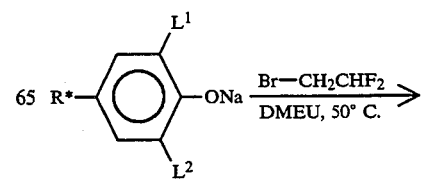

-continued
Scheme 2

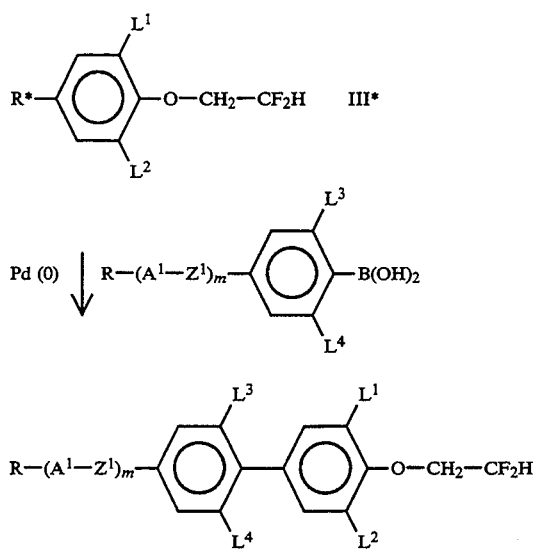

The invention also relates to a process for the preparation of substituted 2,2-difluoroethoxybenzene from the corresponding phenoxide which is distinguished by the fact that the phenoxide is reacted with 1-bromo-2,2-difluoroethane in the presence of an inert solvent. In particular, compounds of the formula III* can be prepared by the process according to the invention. In the compounds of the formula III*, R* is formyl, halogen or a mesogenic group.

The reaction is carried out in the presence of an inert solvent, suitable solvents being the conventional solvents for reactions of phenoxides with alkyl halides, preferably polar aprotic solvents, in particular organic amides, such as, for example, dimethylamide (DMA), hexamethylphosphoric triamide (HMPTA) or N-methylpyrrolidone (NMP) or cyclic urea derivatives, such as, for example, N,N-dimethylpropyleneurea (DMPU) and in particular 1,3-dimethyl-2-imidazolidinone (DMEU).

It is also possible to add cosolvents, such as TMEDA or crown ethers, such as 18-crown-6, to these solvents. The amount of solvent is not crucial, and in general from 100 to 10,000 g of solvent can be used per tool of phenoxide.

The procedure for carrying out the reaction in the process according to the invention is simple; the starting materials can be reacted depending on the phenoxide used, at temperatures of from $-20°$ to $+200°$ C., preferably from $-20°$ to $+150°$ C., and at superatmospheric pressure or reduced pressure, preferably at atmospheric pressure.

The phenoxide is expediently initially introduced in an inert solvent and warmed. 1-Bromo-2,2-difluoroethane is generally added dropwise with stirring over the course of from 0.2 to 24 hours at from $-20°$ C. to $100°$ C., and the mixture is optionally allowed to warm slowly to the boiling point of the solvent.

In general, from 0.8 to 1.5 mol, especially from 0.9 to 1.2 mol, of 1-bromo-2,2-difluoroethane are required per mole of the phenoxide to be reacted.

Work-up of the reaction mixture and isolation of the products are carried out in a conventional manner, for example by pouring the reaction mixture into water and/or ice or dilute acid, separating off the aqueous phase, and isolating the 2,2-difluoroethoxybenzene derivatives by distillation and/or crystallization.

Surprisingly, the process according to the invention allows substituted 2,2-difluoroethoxybenzene derivatives, which are valuable intermediates, for example for liquid crystals, auxiliaries, crop-protection agents and pharmaceuticals, to be prepared in a simple manner compared with the prior art and in higher yields.

Further synthetic methods are evident to the person skilled in the art. For example, appropriately 5-substituted 1,3-difluorobenzene compounds or monofluorinated analogues (n=0, $L^3$=H) can be converted into the 1,3-difluoro compounds or monofluorinated analogues ($L^3$=H) in accordance with the above scheme, and the radical R—($A^1$—$Z^1$) can subsequently be introduced by reactions which are customary in liquid-crystal chemistry (for example esterification, etherification or coupling, for example as described in the article by E. Poetsch, Kontakte (Darmstadt), 1988 (2), p. 15).

The compounds of the formula II where n=0 can be prepared, for example, according to the following synthetic schemes:

Scheme 3

$(A = +A'—Z')_m—A^2)$

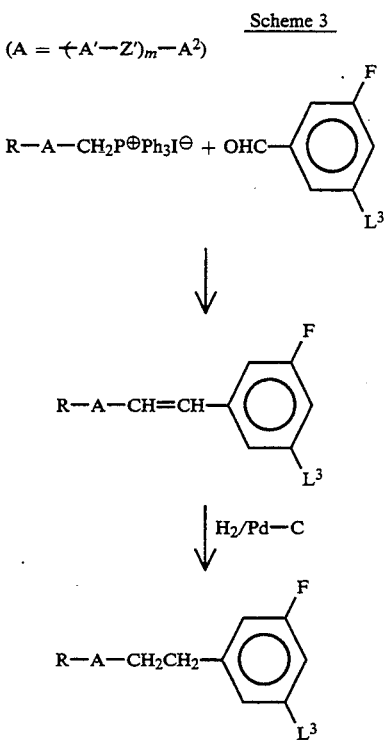

Scheme 4

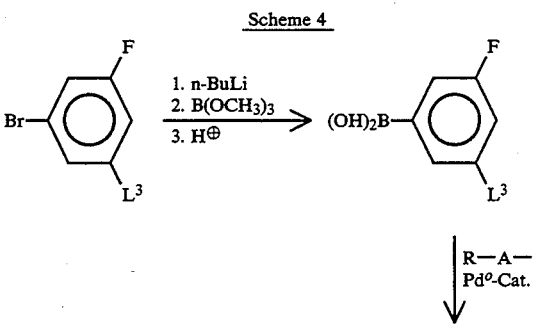

-continued
Scheme 4

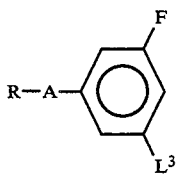

Scheme 5

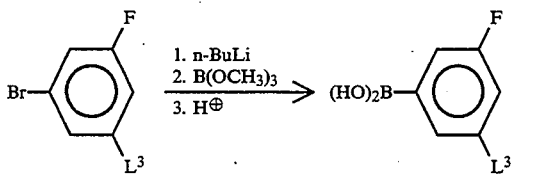

Scheme 6

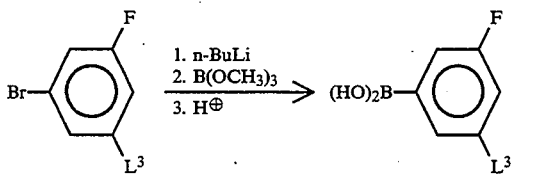

Scheme 7

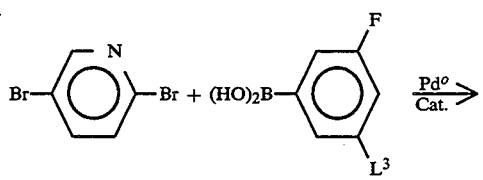

-continued
Scheme 7

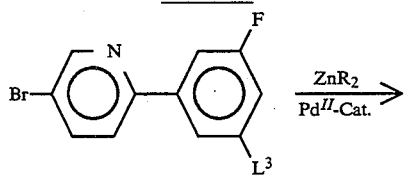

Starting materials are either known or can be prepared analogously to known compounds.

Esters of the formula I can also be obtained by esterifying corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can be prepared analogously to known processes.

In a further process for the preparation of the compounds of the formula I, an aryl halide is reacted with an olefin in the presence of a tertiary amine and in the presence of a palladium catalyst (cf. R. F. Beck, Acc. Chem. Res. 12 (1979) 146).

Examples of suitable aryl halides are chlorides, bromides and iodides, in particular bromides and iodides. The tertiary amines necessary for the success of the coupling reaction, such as, for example, triethylamine, are also suitable as solvent. Examples of suitable palladium catalysts are palladium salts, in particular Pd(II) acetate, with organophosphorus(III) compounds, such as, for example, triarylphosphines. The reaction can be carried out in the presence or absence of an inert solvent at temperatures between about 0° and 150°, preferably between 20° and 100°; examples of suitable solvents are nitriles, such as acetonitriles, or hydrocarbons, such as benzene or toluene. The aryl halides and olefins employed as starting materials are in many cases commercially available or can be prepared by processes known from the literature, for example by halogenation of corresponding parent compounds or by elimination reactions on corresponding alcohols or halides.

In this way, for example, stilbene derivatives can be prepared. The stilbenes can furthermore be prepared by reacting a 4-substituted benzaldehyde with a corresponding phosphorus ylide by the Wittig method. However, tolans of the formula I can also be prepared by employing monosubstituted acetylene instead of the olefin (Synthesis 627 (1980) or Tetrahedron Lett. 27, 1171 1986)).

Aromatic compounds can furthermore be coupled by reacting aryl halides with aryltin compounds. These reactions are preferably carried out with addition of a catalyst, such as, for example, a palladium(0) complex, in inert solvents, such as hydrocarbons, at high temperatures, for example in boiling xylene, under a protective gas.

Coupling reactions of alkynyl compounds with aryl halides can be carried out analogously to the process described by A. O. King, E. Negishi, F. J. Villani and A. Silveira in *J. Org. Chem.* 43, 358 (1978).

Tolans of the formula I can also be prepared by the Fritsch-Buttenberg-Wiechell rearrangement (*Ann.* 279, 319, 1984), in which the 1,1-diaryl-2-haloethylenes are rearranged to diarylacetylenes in the presence of strong bases.

Tolans of the formula I can also be prepared by brominating the corresponding stilbenes and then subjecting the products to dehydrohalogenation. Use may be made here of variants which are known per se, but are not described here in greater detail.

Ethers of the formula I are obtainable by etherifying the corresponding hydroxyl compounds, preferably corresponding phenols, the hydroxyl compound expediently first being converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This can then be reacted with the corresponding alkyl halide, alkyl sulphonate or dialkyl sulphate, expediently in an inert solvent, such as, for example, acetone, 1,2-dimethoxyethane, DMF or dimethyl sulphoxide, or alternatively with an excess of aqueous or aqueous-alcoholic NaOH or KOH, at temperatures between about 20° and 100° C.

The compounds of the formula I in which R=alkenyl can be obtained from the corresponding cyano compounds (R=CN), which are converted into the aldehydes (R=CHO) using diisobutylalumimm For example, in successive steps, a methylene group can be introduced by a Wittig reaction of the aldehyde with methoxymethyltriphenylphosphonium chloride, followed by hydrolysis of the resultant enol ether (for example using dilute hydrochloric acid).

The starting materials are either known or can be prepared analogously to known compounds.

The compounds having a —(CH$_2$)$_4$— bridge can be prepared in accordance with the following scheme:

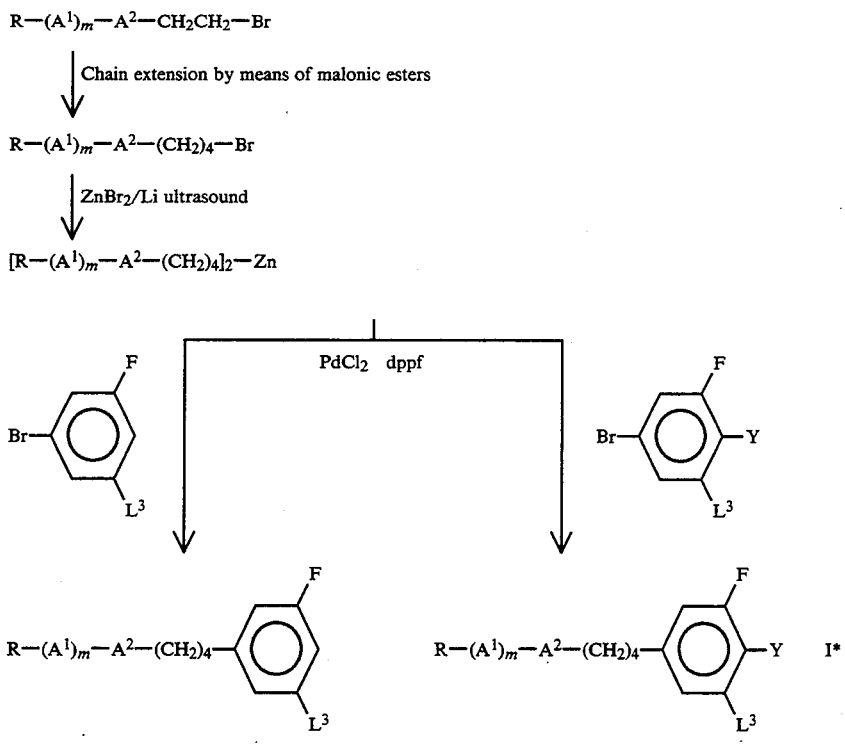

In the Pd(II)-catalysed coupling reaction, either the target product I* is formed directly or a precursor is formed into which the radical -Y is introduced entirely analogously to the above methods for compounds of the formula I.

The compounds having a —CH=CH—CH$_2$CH$_2$— bridge can be prepared by the Wittig method in accordance with the following scheme:

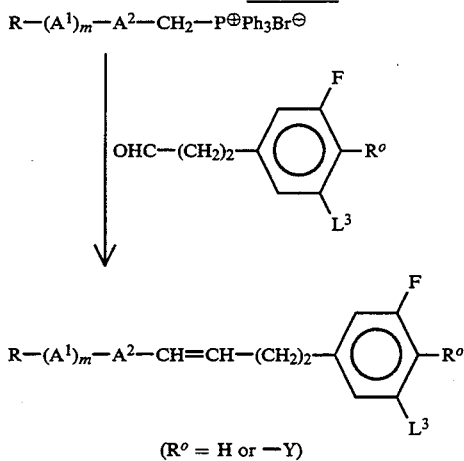

The synthesis of a few particularly preferred compounds is shown in more detail below:

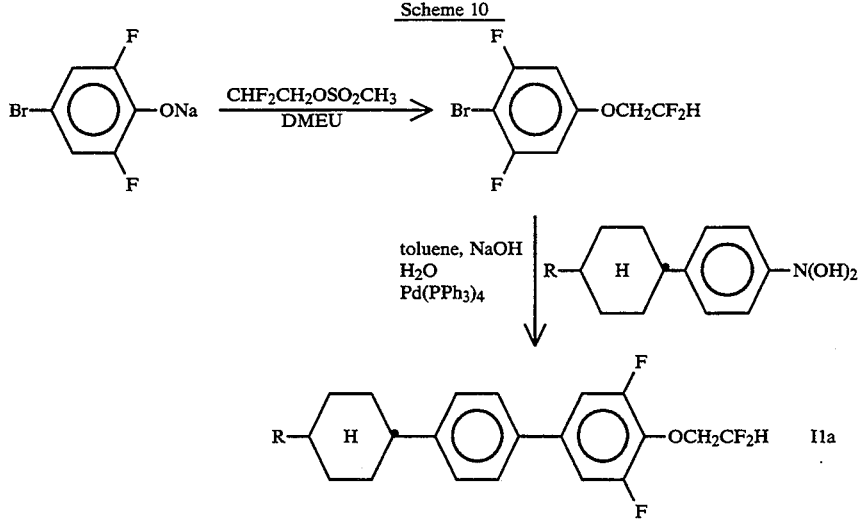

Scheme 10

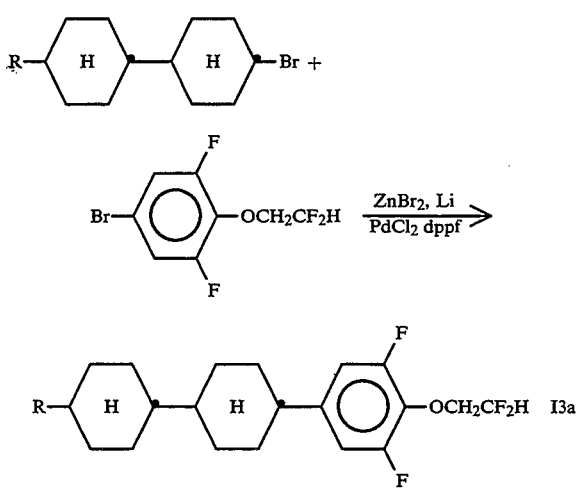

Scheme 11

The invention also relates to electrooptical displays (in particular STN or MLC displays having two plane-parallel outer plates which, together with a frame, form a cell, integrated nonlinear elements for switching individual image points on the outer plates, and a nematic liquid-crystal mixture of positive dielectric anisotropy and high specific resistance located in the cell) which contain media of this type, and to the use of these media for electrooptical purposes.

The liquid-crystal mixtures according to the invention facilitate a significant broadening of the parameter latitude available.

The achievable combinations of clearing point, viscosity at low temperature, thermal and UV stability and dielectric anisotropy are far superior to the previous materials from the prior art.

The requirement for a high clearing point, a nematic phase at low temperature and a high $\Delta\epsilon$ was previously only achievable to an unsatisfactory extent. Although systems such as, for example, ZLI-3119 have a comparable clearing point and comparatively favorable viscosities, they have, however, a $\Delta\epsilon$ of only +3.

Other mixture systems have comparable viscosities and values of $\Delta\epsilon$, but only have clearing points in the region of 60° C.

The liquid-crystal mixtures according to the invention make it possible, while retaining the hematic phase at down to −20° C. and preferably down to −30° C., particularly preferably down to −40° C., to achieve clearing points above 80°, preferably above 90°, particularly preferably above 100° C., simultaneously dielectric anisotropy values $\Delta\epsilon \geq 6$, preferably $\geq 8$, and a high value for the specific resistance, which means that excellent STN and MLC displays can be achieved. The mixtures are characterized in particular by low operating voltages. The TN thresholds (VIP) are below 2.0 V, preferably below 1.5 V, particularly preferably <1.3 V.

It goes without saying that a suitable choice of the components of the mixtures according to the invention also allows higher clearing points (for example above 110°) to be achieved at higher threshold voltages or lower clearing points to be achieved at lower threshold voltages while retaining the other advantageous properties. It is likewise possible to obtain mixtures of relatively high $\Delta\epsilon$ and thus lower thresholds if the viscosities are increased by a correspondingly small amount. The MLC displays according to the invention preferably operate in the first transmission minimum of Gooch and Tarry [C. H. Gooch and H. A. Tarry, Electron. Lett. 10, 2–4, 1974; C. H. Gooch and H. A. Tarry, Appl. Phys., Vol. 8, 1575–1584, 1975]; in this case, a lower dielectric anisotropy in the second minimum is sufficient in addition to particularly favorable electrooptical properties, such as, for example, high gradient of the characteristic line and low angle dependency of the contrast (German Patent 30 22 818) at the same threshold voltage as in an analogous display. This allows significantly higher specific resistances to be achieved in the first minimum using the mixtures according to the invention than using mixtures containing cyano compounds. A person skilled in the art can use simple routine methods to produce the birefringence necessary for a prespecified layer thickness of the MLC display by a suitable choice of the individual components and their proportions by weight.

The viscosity at 20° C. is preferably <60 mPa.s, particularly preferably <50 mPa.s. The nematic phase range is preferably at least 90°, in particular at least 100°. This range preferably extends at least from −20° to 80°.

Measurements of the "capacity holding ratio" (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention containing compounds of the formula I exhibit a considerably smaller decrease in the HR with increasing temperature than do analogous mixtures in which the compounds of the formula I are replaced by cyanophenyl-cyclohexanes of the formula

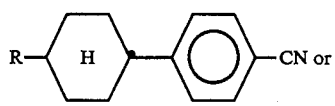

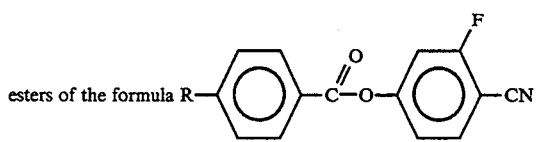

esters of the formula

The UV stability of the mixtures according to the invention is also considerably better, i.e. they exhibit a significantly smaller decrease in the HR on exposure to UV radiation.

The media according to the invention are preferably based on a plurality (preferably two or more) of compounds of the formula I, i.e. the proportion of these compounds is 5–95%, preferably 10–60% and particularly preferably in the range 20–50%.

The individual compounds of the formulae I to XI and their sub-formulae which can be used in the media according to the invention are either known or can be prepared analogously to the known compounds.

Preferred embodiments are indicated below:

medium additionally contains one or more compounds selected from the group comprising the general formulae II to V:

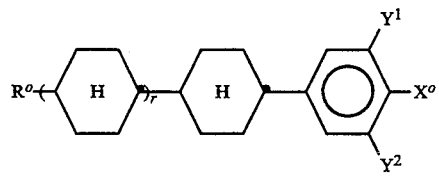 II

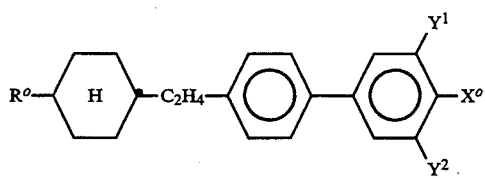 III

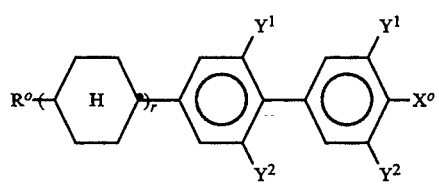 IV

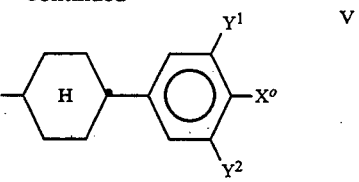 V in which the individual radicals are as defined below:

R⁰: alkyl, oxaalkyl, fluoroalkyl or alkenyl, in each case having 1 to 7 carbon atoms X⁰: F, Cl, CF₃, OCF₃, OCHF₂, OCH=CF₂, OCF=CF₂, OCFH—CF₂H or OCF₂—CF₂H Y¹ and
Y²: each, independently of one another, H or F
r: 0 or 1.

The compound of the formula IV is preferably

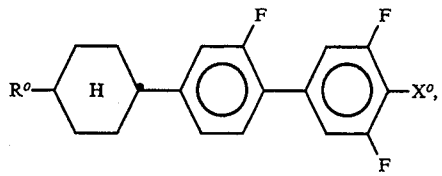

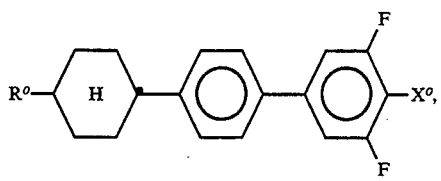

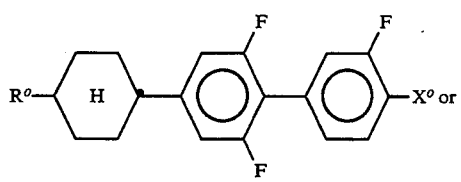

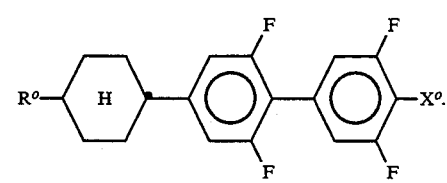

medium additionally contains one or more compounds selected from the group comprising the general formulae VI to XI:

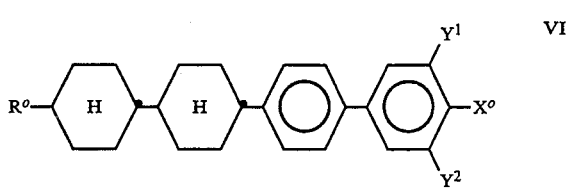 VI

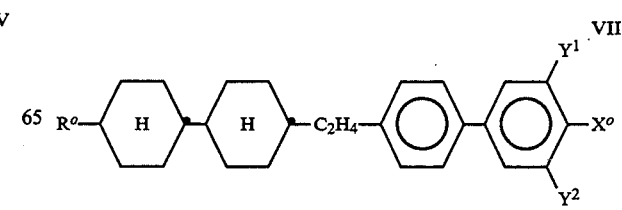 VII

-continued

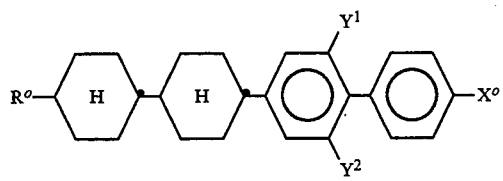 VIII

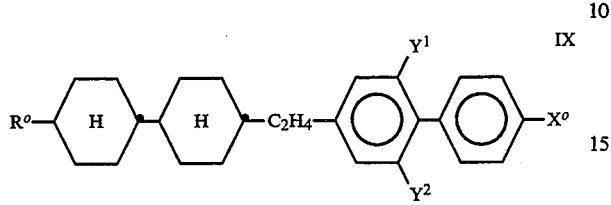 IX

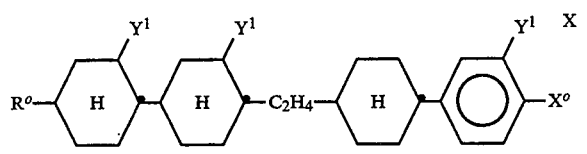 X

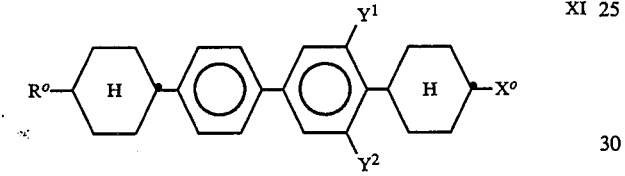 XI in which $R^o$, $Y^1$ and $Y^2$ are each, independently of one another, as defined above, and $X^o$ is F, Cl, CF$_3$, OCF$_3$, OCHF$_2$, alkyl, oxaalkyl, fluoroalkyl or alkenyl, in each case having 1 to 7 carbon atoms.

The proportion of compounds of the formulae I to V together is at least 50% by weight in the total mixture the proportion of compounds of the formula I is from 10 to 50% by weight in the total mixture the proportion of compounds of the formulae II to V is from 30 to 70% by weight in the total mixture

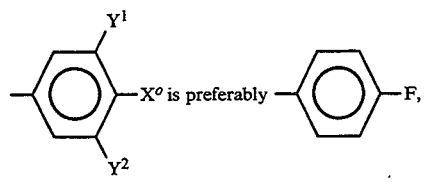

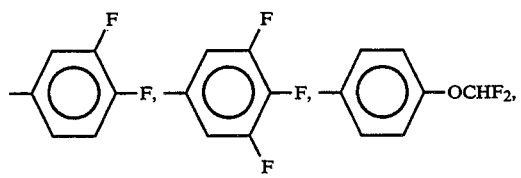

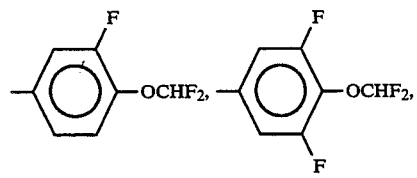

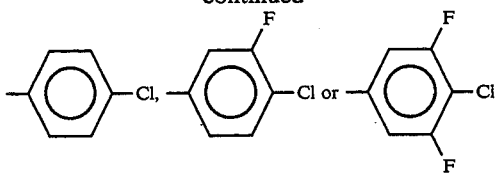

the medium contains compounds of the formulae II, III, IV or V $R^o$ is straight-chain alkyl or alkenyl having 2 to 7 carbon atoms the medium consists essentially of compounds of the formulae I to V the medium contains further compounds, preferably selected from the following group comprising the general formulae XII to XVI:

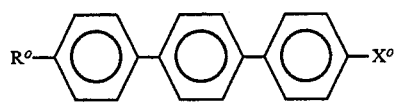 XII

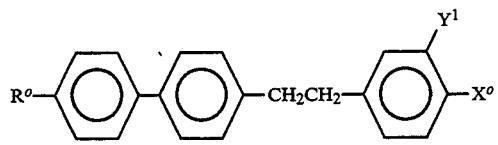 XIII

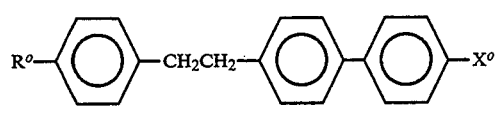 XIV

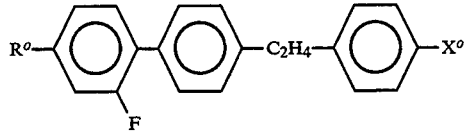 XV ($X^o$ = F or Cl)

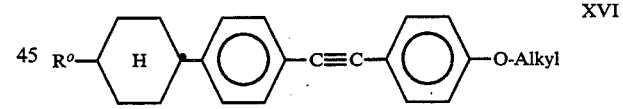 XVI in which $R^o$ and $X^o$ are as defined above and the 1,4-phenylene rings may be substituted by CN, chlorine or fluorine. The 1,4-phenylene rings are preferably mono- or polysubstituted by fluorine atoms.

the I: (II+III+IV+V) weight ratio is preferably from 1:10 to 10:1.

medium consists essentially of compounds selected from the group comprising the general formulae I to XI.

It has been found that even a relatively small proportion of compounds of the formula I mixed with conventional liquid-crystal materials, but in particular with one or more compounds of the formula II, III, IV and/or V, results in a significant lowering of the threshold voltage and in low values for the birefringence, and at the same time broad nematic phases with low smectic-nematic transition temperatures are observed, as a result of which the shelf life is improved. The compounds of the formulae I to V are colorless, stable and readily miscible with one another and with other liquid-crystal materials.

The term "alkyl" covers straight-chain and branched alkyl groups having 1–7 carbon atoms, in particular the straight-chain groups methyl, ethyl, propyl, butyl, pentyl, hexyl and heptyl. Groups having 2–5 carbon atoms are generally preferred.

The term "alkenyl" covers straight-chain and branched alkenyl groups having 2–7 carbon atoms, in particular the straight-chain groups. Preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups containing terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. n is preferably 1 and m is preferably from 1 to 6.

Through a suitable choice of the meanings of $R^o$ and $X^o$, the addressing times, the threshold voltage, the gradient of the transmission characteristic lines, etc., can be modified as desired. For example, 1E-alkenyl radicals, 3E-alkenyl radicals, 2E-alkenyloxy radicals and the like generally give shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals.

A —$CH_2CH_2$— group in $Z^1$ generally results in higher values of $k_{33}/k_{11}$ compared with a simple covalent bond. Higher values of $k_{33}/k_{11}$ facilitate, for example, flatter transmission characteristic lines in TN cells with a 90° twist (for achieving grey tones) and steeper transmission characteristic lines in STN, SBE and OMI cells-(greater multiplexing ability), and vice versa.

The optimum mixing ratio of the compounds of the formulae I and II+III+IV+V depends substantially on the desired properties, on the choice of the components of the formulae I, II, III, IV and/or V and on the choice of any other components which may be present. Suitable mixing ratios within the abovementioned range can easily be determined from case to case.

The total amount of compounds of the formulae I to XI in the mixtures according to the invention is not crucial. The mixtures may therefore contain one or more further components in order to optimize various properties. However, the effect observed on the addressing times and the threshold voltage is generally greater the higher the total concentration of compounds of the formulae I to XI.

In a particularly preferred embodiment, the media according to the invention contain compounds of the formulae II to V (preferably II and/or III) in which $X^o$ is $OCF_3$, $OCHF_2$, F, OCH=$CF_2$, OCF=$CF_2$ or OCF 2—$CF_2H$. A favorable synergistic effect with the compounds of the formula I results in particularly advantageous properties.

For STN applications, the media preferably contain compounds selected from the group comprising the formulae II to V in which $X^o$ is preferably $OCHF_2$ or CN.

The media according to the invention may furthermore contain a component A comprising one or more compounds of the general formula I' having a dielectric anisotropy of from $-1.5$ to $+1.5$

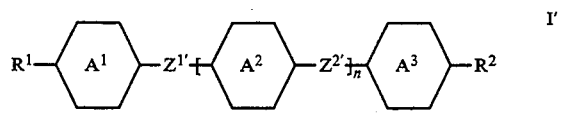

I' in which
$R^1$ and $R^2$ are each, independently of one another, n-alkyl, n-alkoxy, ω-fluoroalkyl or n-alkenyl having 1 to 9 carbon atoms,

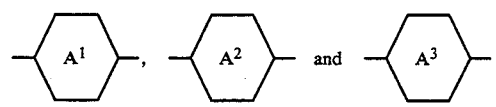

are each, independently of one another, 1,4-phenylene, 2- or 3-fluoro-1,4-phenylene, trans-1,4-cyclohexylene or 1,4-cyclohexenylene,
$Z^{1'}$ and $Z^{2'}$ are each, independently of one another, —$CH_2CH_2$—, —C≡C—, —CO—O—, —O—CO— or a single bond, and
n is 0, 1 or 2.

Component A preferably contains one or more compounds selected from the group comprising II1 to II7:

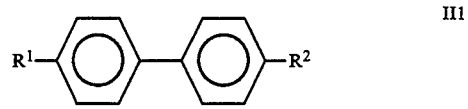

II1

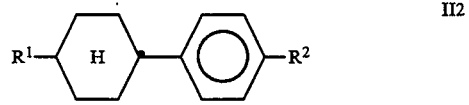

II2

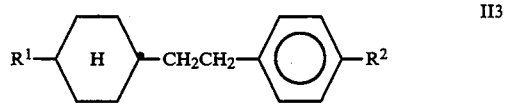

II3

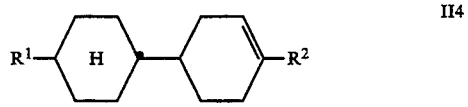

II4

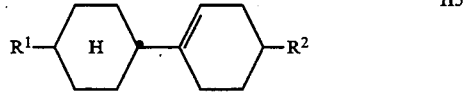

II5

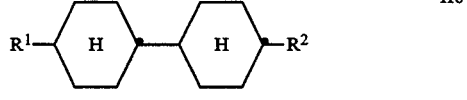

II6

-continued

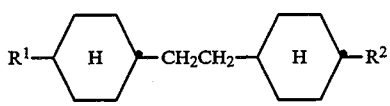
II7 in which R¹ and R² are as defined under the formula I'.

Component A preferably additionally contains one or more compounds selected from the group comprising II8 to II20:

II8

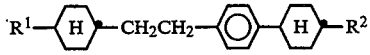
II9

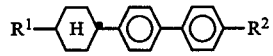
II10

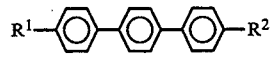
II11

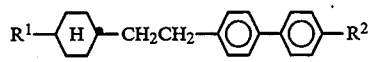
II12

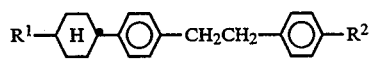
II13

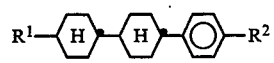
II14

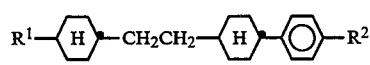
II15

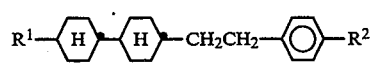
II16

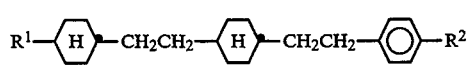
II17

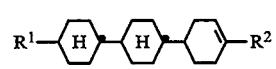
II18

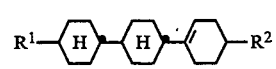
II19

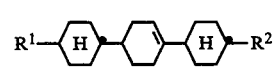
II20 in which R¹ and R² are as defined under the formula I', and the 1,4-phenylene groups in II8 to II17 may each, independently of one another, also be monosubstituted or polysubstituted by fluorine.

Furthermore, component A preferably additionally contains one or more compounds selected from the group comprising II21 to II25:

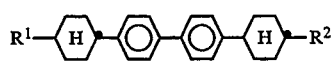
II21

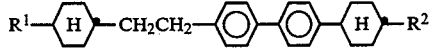
II22

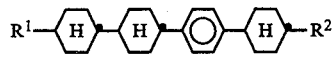
II23

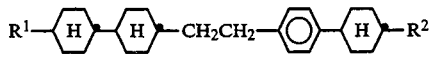
II24

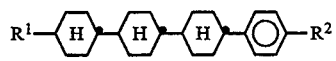
II25 in which R¹ and R² are as defined under the formula I', and the 1,4-phenylene groups in II21 to II25 may also each, independently of one another, be monosubstituted or polysubstituted by fluorine.

The type and amount of the polar compounds having positive dielectric anisotropy is not crucial per se. A person skilled in the art can use simple routine experiments to select suitable materials from the wide range of known and, in many cases, also commercially available components and base mixtures. The media according to the invention preferably contain one or more compounds of the formula I"

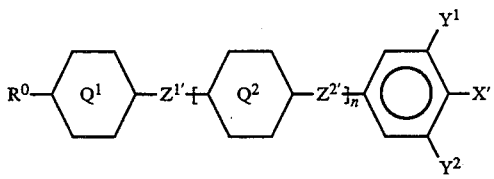
I"

in which $Z^{1'}$, $Z^{2'}$ and n are as defined under the formula I',

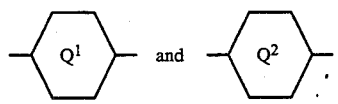

are each, independently of one another, 1,4-phenylene, trans-1,4-cyclohexylene or 3-fluoro-1,4-phenylene, and one of the radicals

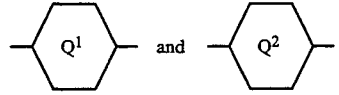

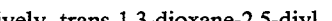

is alternatively trans-1,3-dioxane-2,5-diyl, pyrimidine-2,5-diyl, pyridine-2,5-diyl or 1,4-cyclohexenylene, R° is n-alkyl, n-alkenyl, n-alkoxy or n-oxaalkyl, in each case having 1 to 9 carbon atoms, $Y^1$ or $Y^2$ is H or F and X' is CN, halogen, $CF_3$, $OCF_3$ or $OCHF_2$.

In a preferred embodiment, the media according to the invention for STN or TN applications are based on compounds of the formula I" in which X' is CN. It goes without saying that smaller or larger proportions of other compounds of the formula I" (X'≠CN) are also possible. For MLC applications, the media according to the invention preferably contain only up to about 10% of nitriles of the formula I" (but preferably no nitriles of the formula I", but instead compounds of the formula I' where X' is halogen, $CF_3$, $OCF_3$ or $OCHF_2$). These media are preferably based on the compounds of the formulae II to XI.

The media according to the invention preferably contain one or more compounds having a dielectric anisotropy in the range $-6 \leq \Delta\epsilon \leq -1.5$, of the formula $I'''$

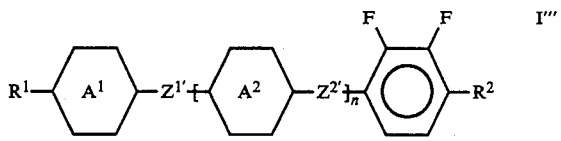

in which $R^1$, $A^1$, $Z^{1'}$, $A^2$, $Z^{2'}$, n and $R^2$ are as defined under formula I', for applications in which a small change in the capacity of the pixel on switching is desired (for example MIM displays or TFT displays).

Preference is given to compounds of the formulae $I^{1'''}$ to $I^{3'''}$:

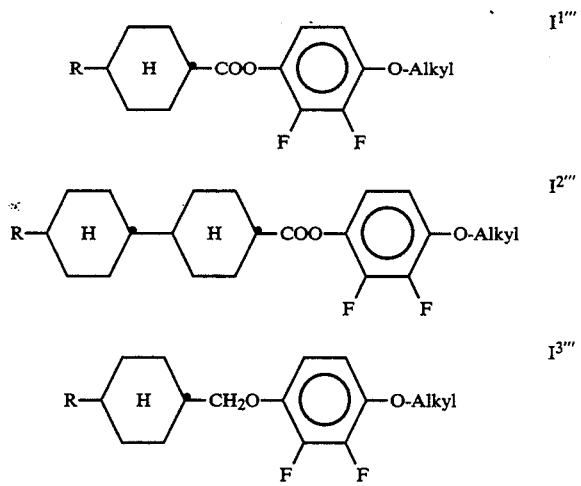

The construction of the STN and MLC displays according to the invention from polarizers, electrode base plates and electrodes with surface treatment corresponds to the construction which is conventional for displays of this type. The term conventional construction here is widely drawn and also covers all derivatives and modifications of the MLC display, in particular also matrix display elements based on poly-Si TFTs or MIMs.

An essential difference between the displays according to the invention and those customary hitherto based on the twisted nematic cell is, however, the choice of liquid-crystal parameters in the liquid-crystal layer.

The liquid-crystal mixtures which can be used according to the invention are prepared in a manner which is conventional per se. In general, the desired amount of the components used in the lesser amount is dissolved in the components making up the principal constituents, expediently at elevated temperature. It is also possible to mix solutions of the components in an organic solvent, for example in acetone, chloroform or methanol, and, after thorough mixing, to remove the solvent again, for example by distillation.

The dielectrics may also contain other additives known to those skilled in the art and described in the literature. For example, 0–15% of pleochroic dyes or chiral dopes can be added.

C denotes a crystalline phase, S a smectic phase, $S_B$ a smectic B phase, N a nematic phase and I the isotropic phase.

$V_{10}$ denotes the voltage for 10% transmission (view angle perpendicular to the plate surface). $t_{on}$ denotes the switch-on time and $t_{off}$ the switch-off time at an operating voltage corresponding to 2.5 times the value of $V_{10}$. $\Delta n$ denotes the optical anisotropy and $n_o$ the refractive index. $\Delta\epsilon$ denotes the dielectric anisotropy ($\Delta\epsilon = \epsilon_\parallel - \epsilon_\perp$, wherein $\epsilon_\parallel$ is the dielectric constant parallel to the longitudinal molecular axes and $\epsilon_\perp$ is the dielectric constant perpendicular thereto). The electrooptical data were measured in a TN cell at the 1st minimum (i.e. at a d.$\Delta n$ value of 0.5) at 20° C., unless expressly stated otherwise. The optical data were measured at 20° C., unless expressly stated otherwise.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application Nos. P 43 15 371.2, filed May 10, 1993, and P 43 38 164.2, filed Nov. 9, 1993, are hereby incorporated by reference.

In the present application and in the examples below, the structures of the liquid-crystal compounds are indicated by acronyms, with the transformation into chemical formulae taking place in accordance with Tables A and B below. All radicals $C_nH_{2n+1}$ and $C_mH_{2m+1}$ are straight-chain alkyl radicals containing n or m carbon atoms. The coding in Table B is self-evident. In Table A, only the acronym for the base structure is given. In individual cases, the acronym for the base structure is followed, separated by a hyphen, by a code for the substituents $R^1$, $R^2$, $L^1$ and $L^2$:

| Code for $R^1$ $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_{3n}H_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF3 | $C_nH_{2n+1}$ | $CF_3$ | H | H |
| nOCF3 | $C_nH_{2n+1}$ | $OCF_3$ | H | H |
| nOCF2 | $C_nH_{2n+1}$ | $OCHF_2$ | H | H |
| nS | $C_nH_{2n+1}$ | NCS | H | H |

-continued
| Code for $R^1$ $R^2$, $L^1$, $L^2$ | $R^1$ | $R^2$ | $L^1$ | $L^2$ |
|---|---|---|---|---|
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | $COOC_mH_{2m+1}$ | H | H |
| nOCCF$_2$.F.F | $C_nH_{2n+1}$ | $OCH_2CF_2H$ | F | F |
TABLE A
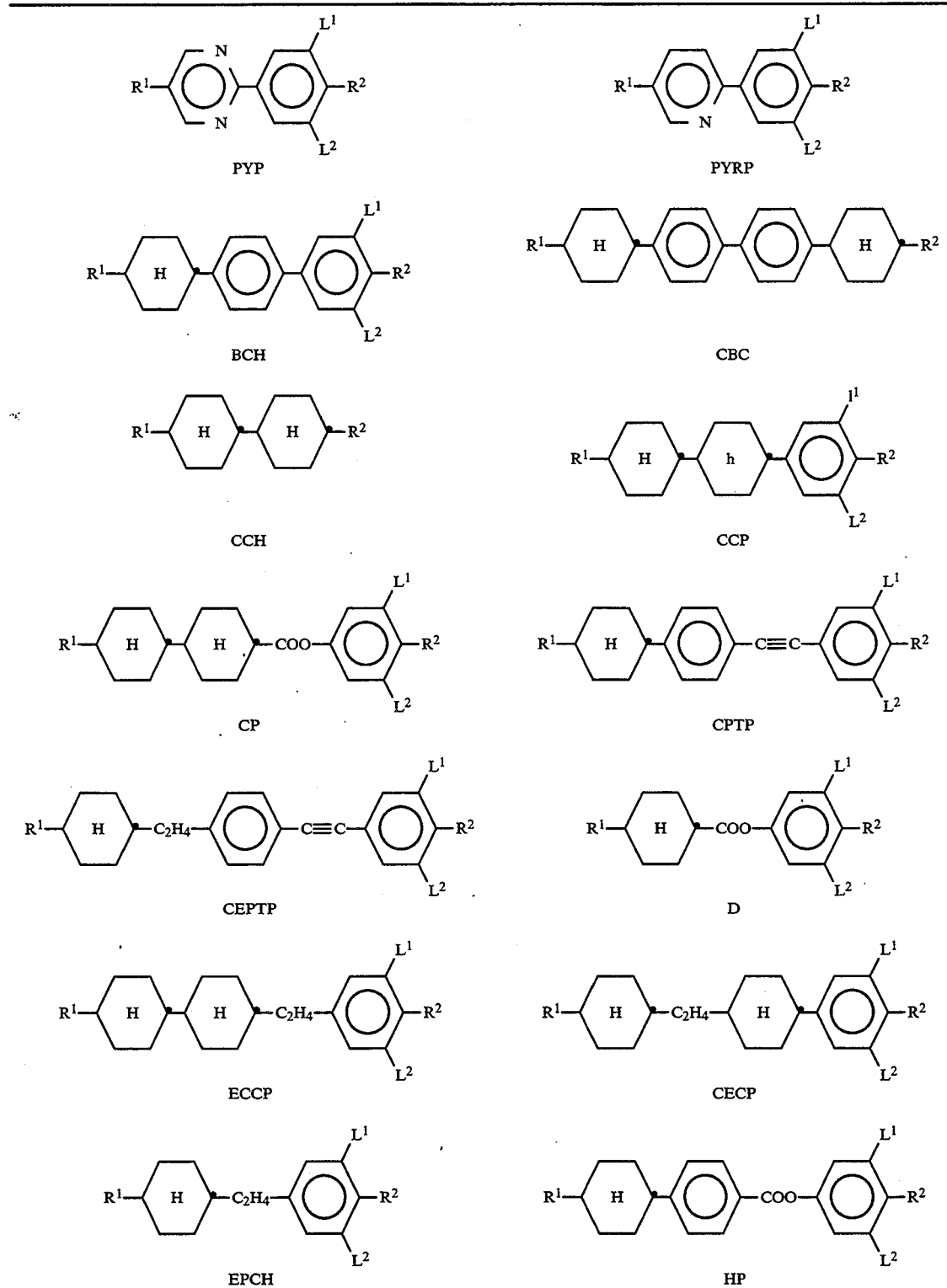

TABLE A-continued
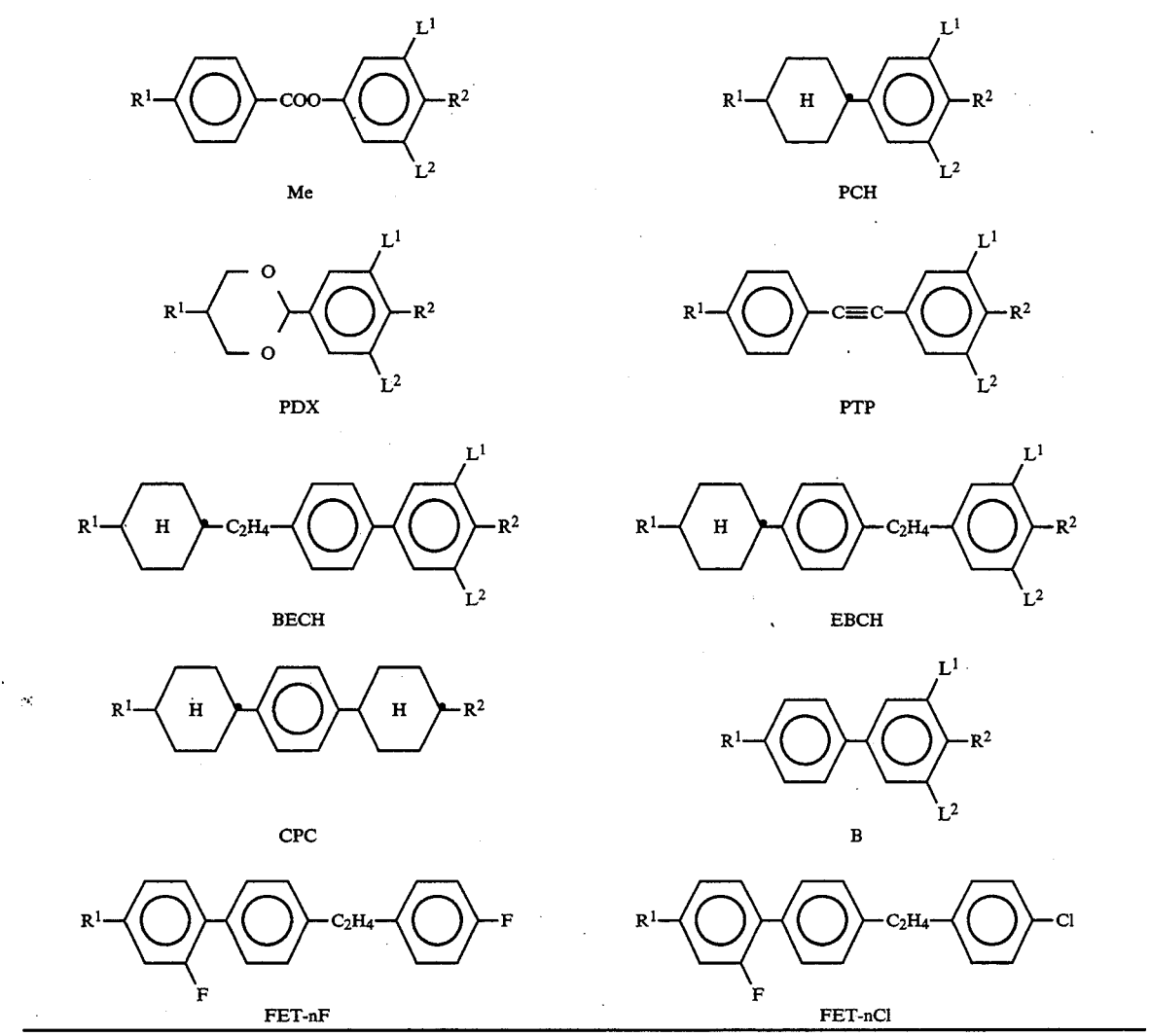
TABLE B
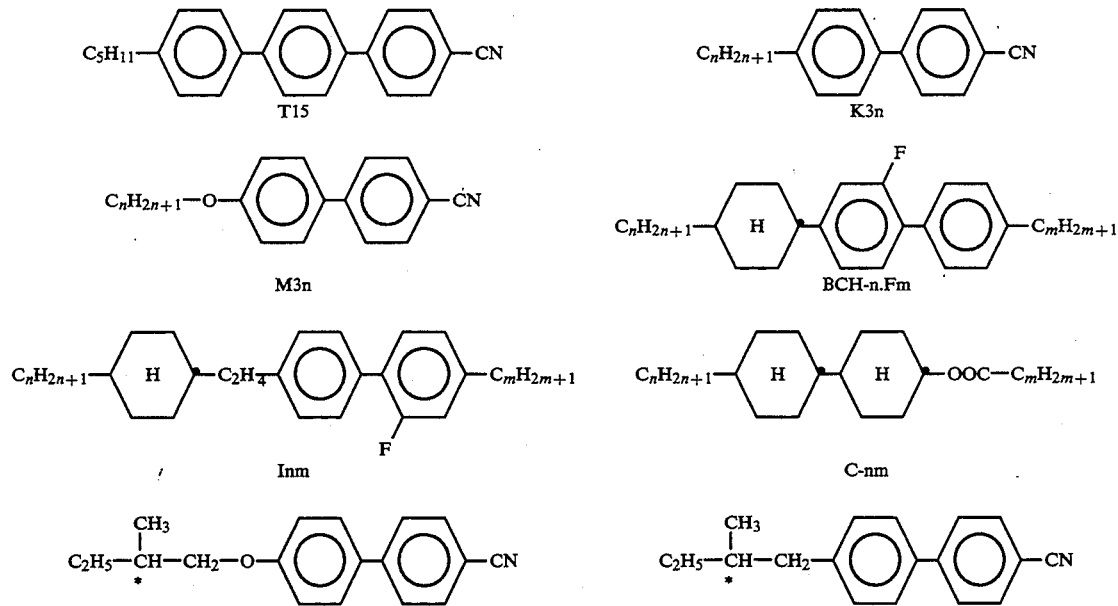

TABLE B-continued

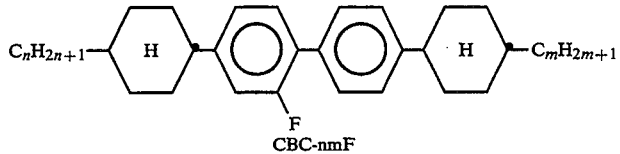

The examples below are intended to illustrate the invention without representing a limitation. Above and below, percentages are by weight. All temperatures are given in degrees Celsius. m.p. denotes melting point, c.p.=clearing point. Furthermore, C=crystalline state, N=nematic phase, S=smectic phase and I=isotropic phase. The numbers between these symbols represent the transition temperatures. Δn denotes optical anisotropy (589 nm, 20° C.) and the viscosity (mm²/sec) was determined at 20° C.

"Conventional work-up" means that, if necessary, water is added, the mixture is extracted with dichloromethane, diethyl ether or toluene, the organic phase is separated off, dried and evaporated, and the product is purified by distillation under reduced pressure or crystallization and/or chromatography. The following abbreviations are used:

DMEU 1,3-dimethyl-2-imidazolidinone
POT potassium tertiary-butoxide
THF tetrahydrofuran
pTSOH p-toluenesulphonic acid

EXAMPLE 1

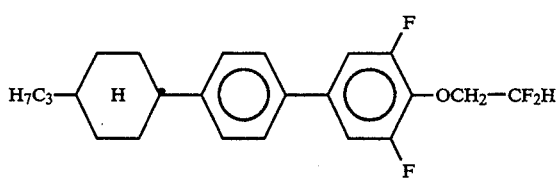

Step 1.1

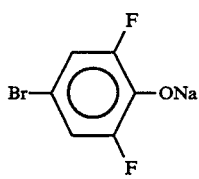

0.05 mol of sodium 1-bromo-3,5-difluorophenoxide in 50 ml of DMEU are introduced into a flask under a nitrogen atmosphere, and the mixture is warmed to 50° C. 0.05 mol of 1-bromo-2,2-difluoroethane are added dropwise with stirring. The mixture is subsequently stirred at 50° C. overnight. 0.005 mol of 1-bromo-2,2-difluoroethane is added, and the mixture is stirred at 70° C. for a further 24 hours and allowed to cool to room temperature, water is added, and the mixture is subjected to customary work-up. b.p. 88°/15 mm.

Step 1.2

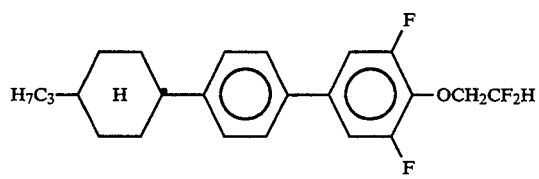

0.03 mol of p-trans-[4-propylcyclohexyl]-phenylboronic acid in 60 ml of toluene are added to 4.8 g of NaOH in 30 ml of water and the mixture is stirred at 45° C. for 0.5 hour. 0.03 mol of 1-(2,2-difluoroethoxy)-4-bromo-2,6-difluorobenzane and 0.7 g of tetrakis(triphenylphosphine)palladium(0) are added to the solution, the mixture is stirred overnight at 100° C. and cooled to room temperature and the organic phase is separated off. The solvent is removed on a rotary evaporator, and the residue is filtered through a silica gel frit with petroleum ether 50°–70°. The filtrate is evaporated, and the residue is recrystallized from n-hexane. C 81 N 121.6 I, Δn=+0.153, Δε=10.41.

The following compounds of the formula

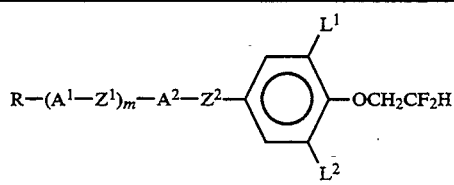

are prepared analogously:

| R | —(A¹—Z¹)ₘ—A²—Z²— | L¹ | L² | |
|---|---|---|---|---|
| C₂H₅ | 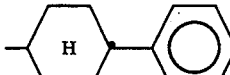 | F | H | |
| C₂H₅ |  | F | F | C 81 N 83.3 I; Δn = +0.148. Δε = 10.38 |
| n-C₃H₇ | 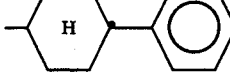 | F | H | C 57 S_B 115 S_A 134 N 156.3 I. Δn = +0.157. Δε = 6.2 |
| n-C₄H₉ |  | F | H | |
| n-C₄H₉ |  | F | F | |

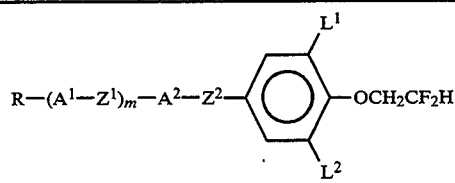
are prepared analogously:
| R | —(A¹—Z¹)ₘ—A²—Z²— | L¹ | L² |
|---|---|---|---|
| n-C₅H₁₁ | Cy-Ph | F | H |
| n-C₆H₁₃ | Cy-Ph | F | H |
| n-C₆H₁₃ | Cy-Ph | F | F |
| H₂C=CHCH₂ | Cy-Ph | F | F |
| C₂H₅ | Ph | F | H |
| C₂H₅ | Ph | F | F |
| n-C₄H₉ | Ph | F | H |
| n-C₄H₉ | Ph | F | F |
| n-C₅H₁₁ | Ph | F | H |
| n-C₅H₁₁ | Ph | F | F |
| n-C₆H₁₃ | Ph | F | H |
| n-C₆H₁₃ | Ph | F | F |

-continued

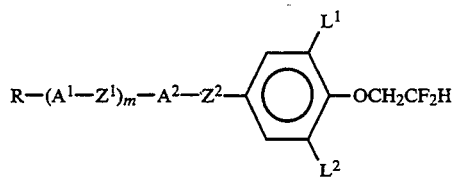

are prepared analogously:

| R | —(A¹—Z¹)$_m$—A²—Z²— | L¹ | L² |
|---|---|---|---|
| n-C$_3$H$_7$ | phenyl-CH$_2$CH$_2$-phenyl | F | H |
| n-C$_3$H$_7$ | phenyl-CH$_2$CH$_2$-phenyl | F | F |
| n-C$_5$H$_{11}$ | phenyl-CH$_2$CH$_2$-phenyl | F | H |
| n-C$_5$H$_{11}$ | phenyl-CH$_2$CH$_2$-phenyl | F | F |
| n-C$_3$H$_7$ | cyclohexyl-CH$_2$CH$_2$-phenyl | F | H |
| n-C$_3$H$_7$ | cyclohexyl-CH$_2$CH$_2$-phenyl | F | F |
| n-C$_5$H$_{11}$ | cyclohexyl-CH$_2$CH$_2$-phenyl | F | H |
| n-C$_5$H$_{11}$ | cyclohexyl-CH$_2$CH$_2$-phenyl | F | F |
| C$_2$H$_5$ | biphenyl | F | H |
| C$_2$H$_5$ | biphenyl | F | F |
| n-C$_3$H$_7$ | biphenyl | F | H |

-continued
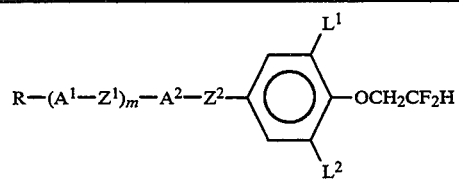
are prepared analogously:
| R | $-(A^1-Z^1)_m-A^2-Z^2-$ | $L^1$ | $L^2$ | |
|---|---|---|---|---|
| n-C₃H₇ | ⬡—⬡ | F | F | |
| n-C₄H₉ | ⬡—⬡ | F | H | |
| n-C₄H₉ | ⬡—⬡ | F | F | |
| n-C₅H₁₁ | ⬡—⬡ | F | H | |
| n-C₅H₁₁ | ⬡—⬡ | F | F | |
| n-C₆H₁₃ | ⬡—⬡ | F | H | |
| n-C₆H₁₃ | ⬡—⬡ | F | F | |
| C₂H₅ | H—⬡(F) | F | H | |
| C₂H₅ | H—⬡(F) | F | F | |
| n-C₃H₇ | H—⬡(F) | F | H | |
| n-C₃H₇ | H—⬡(F) | F | F | C 56 N 97.2 I; Δn +0.139, Δε = 12.34 |

-continued
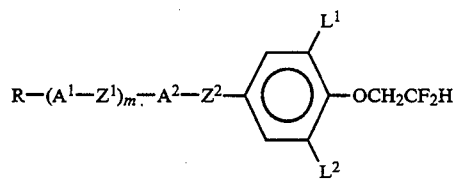
are prepared analogously:
| R | $-(A^1-Z^1)_m-A^2-Z^2-$ | $L^1$ | $L^2$ | |
|---|---|---|---|---|
| n-C$_4$H$_9$ | Cy-Ph(F)- | F | H | |
| n-C$_4$H$_9$ | Cy-Ph(F)- | F | F | |
| n-C$_5$H$_{11}$ | Cy-Ph(F)- | F | H | |
| n-C$_5$H$_{11}$ | Cy-Ph(F)- | F | F | C 35 N 102.5 I; $\Delta n = +0.136$. $\Delta\epsilon = 11.07$ |
| n-C$_6$H$_{13}$ | Cy-Ph(F)- | F | H | |
| n-C$_6$H$_{13}$ | Cy-Ph(F)- | F | F | |
| n-C$_3$H$_7$ | Pyr- | F | H | |
| n-C$_3$H$_7$ | Pyr- | F | F | |
| n-C$_5$H$_{11}$ | Pyr- | F | H | |
| n-C$_5$H$_{11}$ | Pyr- | F | F | |

-continued

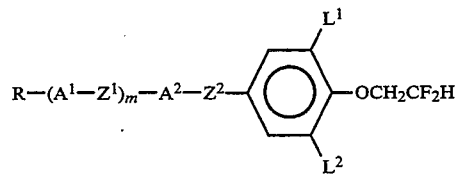

are prepared analogously:

| R | $-(A^1-Z^1)_m-A^2-Z^2-$ | $L^1$ | $L^2$ | |
|---|---|---|---|---|
| n-C$_3$H$_7$ | pyrimidine-phenyl | F | H | |
| n-C$_3$H$_7$ | pyrimidine-phenyl | F | F | |
| n-C$_5$H$_{11}$ | pyrimidine-phenyl | F | H | |
| n-C$_5$H$_{11}$ | pyrimidine-phenyl | F | F | |
| C$_2$H$_5$ | cyclohexyl-difluorophenyl | F | H | |
| C$_2$H$_5$ | cyclohexyl-difluorophenyl | F | F | C 85 I; $\Delta n = +0.135; \Delta\epsilon = 14.1$ |
| n-C$_3$H$_7$ | cyclohexyl-difluorophenyl | F | H | |
| n-C$_3$H$_7$ | cyclohexyl-difluorophenyl | F | F | C 83 N (73.4) I; $\Delta n = +0.122. \Delta\epsilon = 13.43$ |
| n-C$_4$H$_9$ | cyclohexyl-difluorophenyl | F | H | |

-continued

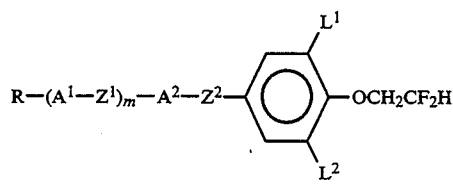

are prepared analogously:

| R | $-(A^1-Z^1)_m-A^2-Z^2-$ | $L^1$ | $L^2$ | |
|---|---|---|---|---|
| n-C$_4$H$_9$ | cyclohexyl—phenyl(F,F) | F | F | C 92 I; $\Delta n = +0.119$; $\Delta\epsilon = 14.2$ |
| n-C$_5$H$_{11}$ | cyclohexyl—phenyl(F,F) | F | H | |
| n-C$_5$H$_{11}$ | cyclohexyl—phenyl(F,F) | F | F | K 82 N 83.6 I; $\Delta n = +0.122$; $\Delta\epsilon = 13.09$ |
| n-C$_6$H$_{13}$ | cyclohexyl—phenyl(F,F) | F | H | |
| n-C$_6$H$_{13}$ | cyclohexyl—phenyl(F,F) | F | F | |
| n-C$_3$H$_7$ | phenyl—phenyl(F) | F | H | |
| n-C$_3$H$_7$ | phenyl—phenyl(F) | F | F | |
| n-C$_5$H$_{11}$ | phenyl—phenyl(F) | F | H | |

-continued
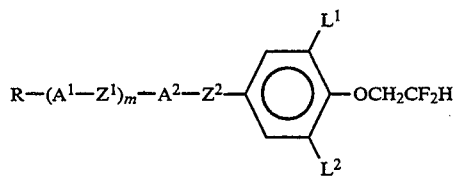
are prepared analogously:
| R | $-(A^1-Z^1)_m-A^2-Z^2-$ | $L^1$ | $L^2$ |
|---|---|---|---|
| n-C$_5$H$_{11}$ | 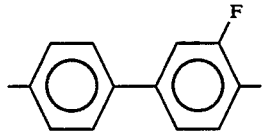 | F | F |
| n-C$_3$H$_7$ | 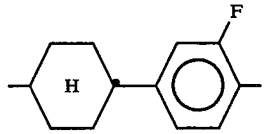 | F | H |
| n-C$_3$H$_7$ | 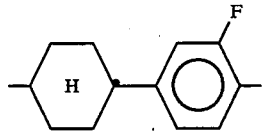 | F | F |
| n-C$_5$H$_{11}$ | 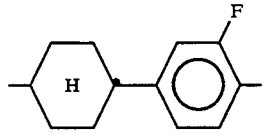 | F | H |
| n-C$_5$H$_{11}$ | 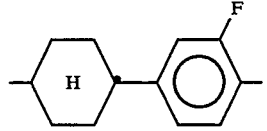 | F | F |
| n-C$_3$H$_7$ | 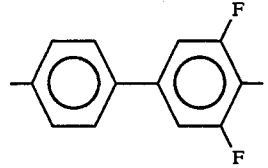 | F | H |
| n-C$_3$H$_7$ | 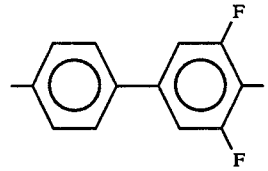 | F | F |
| n-C$_5$H$_{11}$ | 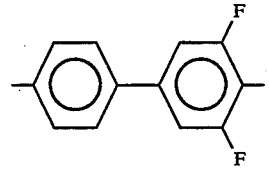 | F | H |

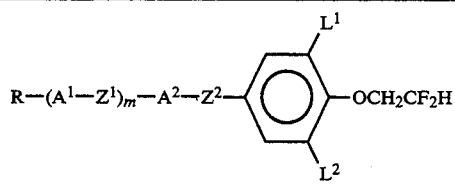
are prepared analogously:
| R | —(A¹—Z¹)ₘ—A²—Z²— | L¹ | L² |
|---|---|---|---|
| n-C₅H₁₁ | [biphenyl with 3,5-difluoro] | F | F |
| n-C₃H₇ | [1,3-dioxane-phenyl] | F | H |
| n-C₃H₇ | [1,3-dioxane-phenyl] | F | F |
| n-C₅H₁₁ | [1,3-dioxane-phenyl] | F | H |
| n-C₅H₁₁ | [1,3-dioxane-phenyl] | F | F |
| C₂H₅ | [cyclohexyl] | H | H |
| n-C₃H₇ | [cyclohexyl] | H | H |
| n-C₅H₁₁ | [cyclohexyl] | H | H |
| C₂H₅ | [bicyclohexyl] | H | H |
| n-C₃H₇ | [bicyclohexyl] | H | H |
| n-C₅H₁₁ | [bicyclohexyl] | H | H |

-continued

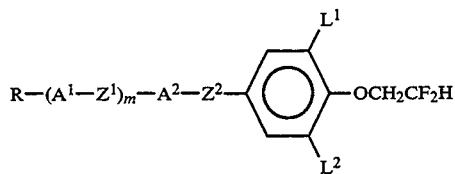

are prepared analogously:

| R | —(A¹—Z¹)$_m$—A²—Z²— | L¹ | L² | |
|---|---|---|---|---|
| C₂H₅ | cyclohexyl-phenyl | H | H | |
| n-C₃H₇ | cyclohexyl-phenyl | H | H | |
| n-C₅H₁₁ | cyclohexyl-phenyl | H | H | C 94 S$_B$ 168 S$_A$ 194 N 200.3 I; Δn = +0.172; Δε = 4.52 |

EXAMPLE 2

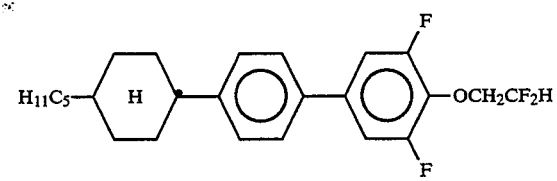

Step 2.1 HCF₂CH₂OSO₂CH₃

4.0 ml of 2,2-difluoroethanol are dissolved in 200 ml of dichloromethane, and 4.04 mol of triethylamine are added dropwise at 10°–15° C. The mixture is subsequently stirred for 10 minutes, and 4.04 mol of methanesulphonyl chloride are added dropwise at 5°–10° C. The reaction mixture is stirred overnight, during which a white precipitate forms. The precipitate is filtered off, and the filtrate is washed with 10% hydrochloric acid and then with water. The solution is subsequently dried over sodium sulphate and evaporated, and the residue is distilled. b.p. 172° C./100 mm.

Step 2.2

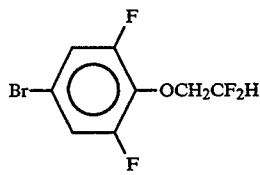

0.42 mol of 4-bromo-2,6-difluorophenoxide are dissolved in 350 ml of DMEU under nitrogen, and the mixture is heated to 140° C. 0.42 mol of the mesylate from step 2.1 is added dropwise over the course of 0.5 hour, and the mixture is stirred at 140° C. overnight. The reaction mixture is allowed to cool and is introduced into 2 l of water. After extraction with ether, the ether phases are washed first with 5% sodium hydroxide solution and subsequently with water and are dried over sodium sulphate. The solution is evaporated, and the residue is distilled. b.p. 88°–89° C./15 mm.

Step 2.3

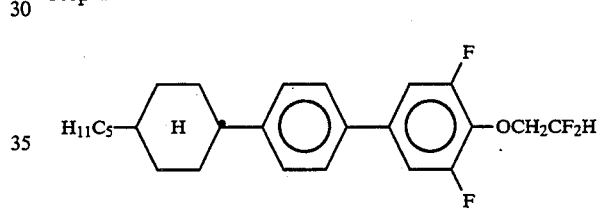

The coupling of p-trans-(4-pentylcyclohexyl)phenylboronic acid with 1-(2,2-difluoroethoxy)-4-bromo-2,6-difluorobenzene is carried out analogously to step 1.2. C 54 N 122.7 I; Δn=+0.147; Δε=9.85.

EXAMPLE 3

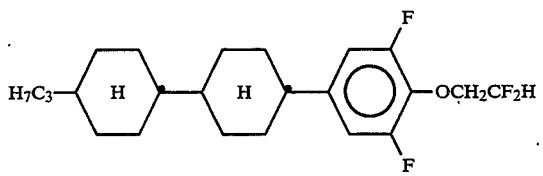

0.1 mol of trans-4-(trans-4-propylcyclohexyl)cyclohexyl bromide, 0.2 mol of lithium granules and 0.05 mol of zinc bromide in 150 ml of toluene/THF (4:1) are treated with ultrasound for 4 hours at 10-15° C. 0.05 mol of 1-(2,2-difluoroethoxy)-4-bromo-2,6-difluorobenzene and 1.2 g of 1,1'-bis(diphenylphosphine)ferrocenepalladium(II) chloride are added, and the mixture is stirred at room temperature overnight. 200 ml of saturated ammonium chloride solution are added dropwise to the solution, which is then stirred for 0.5 hour. The organic phase is separated off, and the aqueous phase is extracted with toluene. The combined organic extracts are dried over sodium sulphate. C 72 N 152.9 I, Δn=+0.087, Δε=7.75.

The following compounds of the formula

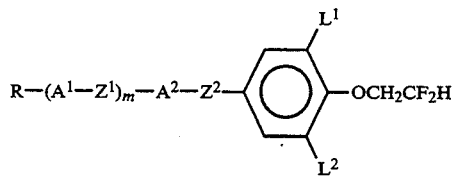

are prepared analogously:

| R | —(A¹—Z¹)ₘ—A²—Z²— | L¹ | L² | |
|---|---|---|---|---|
| C$_2$H$_5$ | -[H]-[H]- | F | H | |
| C$_2$H$_5$ | -[H]-[H]- | F | F | C 47 N 117.7 I; Δn = +0.085. Δε = 7.26 |
| n-C$_4$H$_9$ | -[H]-[H]- | F | H | |
| n-C$_4$H$_9$ | -[H]-[H]- | F | F | |
| n-C$_5$H$_{11}$ | -[H]-[H]- | F | H | |
| n-C$_5$H$_{11}$ | -[H]-[H]- | F | F | C 54 N 155.2 I; Δn = +0.089. Δε = 7.79 |
| n-C$_6$H$_{13}$ | -[H]-[H]- | F | F | |
| CH$_2$=CHCH$_2$ | -[H]-[H]- | F | F | |
| n-C$_7$H$_{15}$ | -[H]-[H]- | F | H | |
| n-C$_7$H$_{15}$ | -[H]-[H]- | F | F | |
| C$_2$H$_5$ | -[H]- | F | H | |
| C$_2$H$_5$ | -[H]- | F | F | |
| n-C$_3$H$_7$ | -[H]- | F | H | |
| n-C$_3$H$_7$ | -[H]- | F | F | |
| n-C$_5$H$_{11}$ | -[H]- | F | H | |
| n-C$_5$H$_{11}$ | -[H]- | F | F | |
| n-C$_6$H$_{13}$ | -[H]- | F | F | |
| CH$_2$=CHCH$_2$ | -[H]- | F | F | |
| n-C$_3$H$_7$ | -[H]-C$_2$H$_4$-[H]- | F | H | |
| n-C$_3$H$_7$ | -[H]-C$_2$H$_4$-[H]- | F | F | |
| n-C$_5$H$_{11}$ | -[H]-C$_2$H$_4$-[H]- | F | H | |
| n-C$_5$H$_{11}$ | -[H]-C$_2$H$_4$-[H]- | F | F | |
| CH$_2$=CHCH$_2$ | -[H]-C$_2$H$_4$-[H]- | F | H | |
| CH$_2$=CHCH$_2$ | -[H]-C$_2$H$_4$-[H]- | F | F | |
| n-C$_3$H$_7$ | -[H]-[H]- | H | H | |
| n-C$_5$H$_{11}$ | -[H]-[H]- | H | H | |

Comparison of the viscosities (ν 20° C.) and the phase ranges (ΔT) as a function of the degree of fluorination

| Compound | ν 20° C. [mm²/s] | ΔT (N) |
|---|---|---|
| H$_{11}$C$_5$-[H]-[Ph]-[Ph]-O-CH$_2$-CHF$_2$ | 66 | — |
| H$_{11}$C$_5$-[H]-[Ph]-[Ph(F)]-O-CH$_2$-CHF$_2$ | 45 | 40.6° C. |
| H$_{11}$C$_5$-[H]-[Ph]-[Ph(F,F)]-O-CH$_2$-CHF$_2$ | 23 | 68.7° C. |

Mixture examples

Example I

| | | | |
|---|---|---|---|
| PCH-5F | 5.0% | S → N [°C.]: | |
| PCH-7F | 6.0% | Clearing point [°C.]: | +98 |
| CCP-2OCF$_3$ | 11.0% | Δn [589 nm, 20° C.]: | +0.0976 |

-continued

Mixture examples

| | | | |
|---|---|---|---|
| CCP-3OCF$_3$ | 12.0% | Δε [1 kHz, 20° C.]: | |
| CCP-4OCF$_3$ | 10.0% | V$_{(10,0,20)}$ [V]: | 1.53 |
| CCP-5OCF$_3$ | 12.0% | V$_{(90,0,20)}$ [V]: | 2.43 |
| BCH-3F.F.F | 12.0% | | |
| BCH-5F.F.F | 11.0% | | |
| CCP-3OCCF$_2$.F.F | 12.0% | | |
| CCP-5OCCF$_2$.F.F | 9.0% | | |
| Example II | | | |
| PCH-5F | 5.0% | S → N [°C.]: | <0 |
| PCH-7F | 6.0% | Clearing point [°C.]: | +107 |
| CCP-2OCF$_3$ | 11.0% | Δn [589 nm, 20° C.]: | +0.0836 |
| CCP-3OCF$_3$ | 12.0% | V$_{(10,0,20)}$ [V]: | 1.67 |
| CCP-4OCF$_3$ | 10.0% | V$_{(90,0,20)}$ [V]: | 2.66 |
| CCP-5OCF$_3$ | 12.0% | | |
| BCH-3OCCF$_3$.F.F | 12.0% | | |
| BCH-5OCCF$_3$F.F.F | 11.0% | | |
| CCP-3F.F.F | 12.0% | | |
| CCP-5F.F.F | 9.0% | | |
| Example III | | | |
| PCH-5F | 5.0% | S → N [°C.]: | <0 |
| PCH-7F | 6.0% | Clearing point [°C.]: | +112 |
| CCP-2OCF$_3$ | 11.0% | Δn [589 nm, 20° C.]: | +0.1016 |
| CCP-3OCF$_3$ | 12.0% | V$_{(10,0,20)}$ [V]: | 1.65 |
| CCP-4OCF$_3$ | 10.0% | V$_{(90,0,20)}$ [V]: | 2.60 |
| CCP-5OCF$_3$ | 12.0% | | |
| BCH-3OCCF$_2$.F.F | 12.0% | | |
| BCH-5OCCF$_2$.F.F | 11.0% | | |
| CCP-3OCCF$_2$.F.F | 12.0% | | |
| CCP-5OCCF$_2$.F.F | 9.0% | | |
| Example IV | | | |
| BCH-3OCCF$_2$.F.F | 25.0% | S → N [°C.]: | |
| CCP-3OCCF$_2$.F.F | 25.0% | Δn [589 nm, 20° C.]: | +135 |
| CCP-5OCCF$_2$.F.F | 25.0% | V$_{(10,0,20)}$ [V]: | +0.1308 |
| | | V$_{(90,0,20)}$ [V]: | |
| Example 5 | | | |
| PCH-5F | 10.0% | S → N [°C.]: | |
| BCH-3OCCF$_2$.F.F | 22.5% | Clearing point [°C.]: | +111 |
| BCH-5OCCF$_2$.F.F | 22.5% | Δn [589 nm, 20° C.]: | +0.1200 |
| CCP-3OCCF$_2$.F.F | 22.5% | V$_{(10,0,20)}$ [V]: | |
| CCP-5OCCF$_2$.F.F | 22.5% | V$_{(90,0,20)}$ [V]: | |
| Example VI | | | |
| PCH-5F | 10.0% | S → N [°C.]: | |
| BCH-3OCCF$_2$.F.F | 22.5% | Clearing point [°C.]: | +92 |
| BCH-5OCCF$_2$.F.F | 22.5% | Δn [589 nm, 20° C.]: | +0.1105 |
| CCP-3OCCF$_2$.F.F | 22.5% | V$_{(10,0,20)}$ [V]: | 1.53 |
| CCP-5OCCF$_2$.F.F | 22.5% | V$_{(50,0,20)}$ [V]: | 1.90 |
| | | V$_{(90,0,20)}$ [V]: | 2.38 |
| Example VII | | | |
| PCH-5F | 10.0% | S → N [°C.]: | |
| BCH-3OCF$_2$.F.F | 22.5% | Clearing point [°C.]: | +88 |
| BCH-5OCF$_2$.F.F | 22.5% | Δn [589 nm, 20° C.]: | +0.0810 |
| CCP-3OCCF$_2$.F.F | 22.5% | V$_{(10,0,20)}$ [V]: | 1.50 |
| CCP-5OCCF$_2$.F.F | 22.5% | V$_{(50,0,20)}$ [V]: | 1.88 |
| | | V$_{(90,0,20)}$ [V]: | 2.37 |
| Example VIII | | | |
| PCH-5F | 10.0% | S → N [°C.]: | |
| BCH-3OCF$_3$.F.F | 22.5% | Clearing point [°C.]: | +82 |
| BCH-5OCF$_3$.F.F | 22.5% | Δn [589 nm, 20° C.]: | +0.0779 |
| CCP-3OCCF$_2$.F.F | 22.5% | V$_{(10,0,20)}$ [V]: | 1.44 |
| CCP-5OCCF$_2$.F.F | 22.5% | V$_{(50,0,20)}$ [V]: | 1.70 |
| | | V$_{(90,0,20)}$ [V]: | 2.25 |
| Example IX | | | |
| PCH-6F | 4.5% | S → N [°C.]: | <−40 |
| PCH-7F | 4.0% | Clearing point [°C.]: | +84 |
| CCP-2OCF$_2$.F.F | 16.0% | Δn [589 nm, 20° C.]: | +0.1012 |
| CCP-3OFC$_2$.F.F | 15.0% | V$_{10,0,20}$ [V]: | 1.17 |
| CCP-5OCF$_2$.F.F | 16.0% | V$_{(50,0,20)}$ [V]: | 1.47 |
| CUP.2F.F | 6.0% | V$_{(90,0,20)}$ [V]: | 1.87 |
| CUP.3F.F | 6.0% | ν 20: | 44 cSt |
| CUP-5F.F | 5.0% | ν −40: | 19000 cSt |
| CUP-3OCCF$_2$.F.F | 9.0% | HR (100° C.): | 92% |
| CUP.5OCCF$_2$.F.F | 9.0% | | |
| CBC-33F | 3.5% | | |
| CBC-53F | 3.5% | | |
| CBC-55F | 3.0% | | |
| Example X | | | |
| PCH-5F | 3.0% | S → N [°C.]: | |
| CCP-2OCF$_2$.F.F | 16.0% | Clearing point [°C.]: | +109 |
| CCP-3OCF$_2$.F.F | 15.0% | Δn [589 nm, 20° C.]: | +0.1111 |

-continued

Mixture examples

| | | | |
|---|---|---|---|
| CCP-5OCF₂.F.F | 16.0% | Δε [1 kHz, 20° C.]: | |
| CUP.2F.F | 5.0% | V$_{(10,0,20)}$ [V]: | 1.29 |
| CUP-3F.F | 5.0% | V$_{(90,0,20)}$ [V]: | 2.03 |
| CUP-5F.F | 5.0% | | |
| CUP-3OCCF₂.F.F | 10.0% | | |
| CUP-5OCCF₂.F.F | 10.0% | | |
| CBC-33F | 5.0% | | |
| CBC-53F | 5.0% | | |
| CBC-55F | 5.0% | | |

Example XI

| | | | |
|---|---|---|---|
| PCH-5F | 6.0% | S → N [°C.]: | |
| CCP-2OCF₂.F.F | 16.0% | Clearing point [°C.]: | +96 |
| CCP-3OCF₂.F.F | 15.0% | Δn [589 nm, 20° C.]: | +0.1061 |
| CCP-5OCF₂.F.F | 16.0% | Δε [1 kHz, 20° C.]: | |
| CUP.2F.F | 5.0% | V$_{(10,0,20)}$ [V]: | 1.24 |
| CUP-3F.F | 5.0% | V$_{(90,0,20)}$ [V]: | 1.92 |
| CUP-5F.F | 5.0% | | |
| CUP-3OCCF₂.F.F | 10.0% | | |
| CUP-5OCCF₂.F.F | 10.0% | | |
| CBC-33F | 4.0% | | |
| CBC-53F | 4.0% | | |
| CBC-55F | 4.0% | | |

Example XII

| | | | |
|---|---|---|---|
| PCH-5F | 5.0% | S → N [°C.]: | |
| CCP-2OCF₂.F.F | 16.0% | Clearing point [°C.]: | +100 |
| CCP-3OCF₂.F.F | 15.0% | Δn [589 nm, 20° C.]: | +0.1077 |
| CCP-5OCF₂.F.F | 16.0% | Δε [1 kHz, 20° C.]: | |
| CUP.2F.F | 5.0% | V$_{(10,0,20)}$ [V]: | 1.25 |
| CUP-3F.F | 5.0% | V$_{(90,0,20)}$ [V]: | 1.97 |
| CUP-5F.F | 5.0% | | |
| CUP-3OCCF₂.F.F | 10.0% | | |
| CUP-5OCCF₂.F.F | 10.0% | | |
| CBC-33F | 5.0% | | |
| CBC-53F | 4.5% | | |
| CBC-55F | 3.5% | | |

Example XIII

| | | | |
|---|---|---|---|
| PCH-6F | 3.5% | S → N [°C.]: | |
| PCH-7F | 3.0% | Clearing point [°C.]: | +88 |
| CCP-2OCF₂.F.F | 16.0% | Δn [589 nm, 20° C.]: | +0.1036 |
| CCP-3OCF₂.F.F | 15.0% | Δε [1 kHz, 20° C.]: | |
| CCP-5OCF₂.F.F | 16.0% | V$_{(10,0,20)}$ [V]: | 1.14 |
| CUP-2F.F | 6.0% | V$_{(90,0,20)}$ [V]: | 1.79 |
| CUP-3F.F | 6.0% | | |
| CUP-5F.F | 5.0% | | |
| CUP-3OCCF₂.F.F | 10.0% | | |
| CUP-5OCCF₂.F.F | 10.0% | | |
| CBC-33F | 3.5% | | |
| CBC-53F | 3.0% | | |
| CBC-55F | 3.0% | | |

Example XIV

| | | | |
|---|---|---|---|
| PCH-6F | 5.5% | S → N [°C.]: | |
| PCH-7F | 53.0% | Clearing point [°C.]: | +81 |
| CCP-2OCF₂.F.F | 16.0% | Δn [589 nm, 20° C.]: | +0.0994 |
| CCP-3OCF₂.F.F | 15.0% | Δε [1 kHz, 20° C.]: | |
| CCP-5OCF₂.F.F | 16.0% | V$_{(10,0,20)}$ [V]: | 1.21 |
| CUP-2F.F | 5.0% | V$_{(90,0,20)}$ [V]: | 1.88 |
| CUP-3F.F | 5.0% | | |
| CUP-5F.F | 5.0% | | |
| CUP-3OCCF₂.F.F | 9.0% | | |
| CUP-5OCCF₂.F.F | 9.0% | | |
| CBC-33F | 3.5% | | |
| CBC-53F | 3.0% | | |
| CBC-55F | 3.0% | | |

Example XV

| | | | |
|---|---|---|---|
| PCH-6F | 4.5% | S → N [°C.]: | <−40 |
| PCH-7F | 4.0% | Clearing point [°C.]: | +84 |
| CCP-2OCF₂.F.F | 16.0% | Δn [589 nm, 20° C.]: | +0.1012 |
| CCP-3OCF₂.F.F | 15.0% | Δε [1 kHz, 20° C.]: | |
| CCP-5OCF₂.F.F | 16.0% | V$_{(10,0,20)}$ [V]: | 1.18 |
| CUP-2F.F | 6.0% | V$_{(90,0,20)}$ [V]: | 1.87 |
| CUP-3F.F | 6.0% | | |
| CUP-5F.F | 5.0% | | |
| CUP-3OCCF₂.F.F | 9.0% | | |
| CUP-5OCCF₂.F.F | 9.0% | | |
| CBC-33F | 3.5% | | |
| CBC-53F | 3.0% | | |
| CBC-55F | 3.0% | | |

Example XVI

| | | | |
|---|---|---|---|
| PCH-6F | 4.5% | S → N [°C.]: | <−40 |

-continued

Mixture examples

| | | | |
|---|---|---|---|
| PCH-7F | 4.0% | Clearing point [°C.]: | +93 |
| CCP-2OCF$_2$.F.F | 8.0% | Δn [589 nm, 20° C.]: | +0.1036 |
| CCP-3OCF$_2$.F.F | 8.0% | Δε [1 kHz, 20° C.]: | |
| CCP-5OCF$_2$.F.F | 8.0% | V$_{(10,0,20)}$ [V]: | 1.21 |
| CCP-2OCCF$_2$.F.F | 8.0% | V$_{(90,0,20)}$ [V]: | 1.92 |
| CCP-3OCCF$_2$.F.F | 7.0% | | |
| CCP-5OCCF$_2$.F.F | 8.0 | | |
| CUP-2F.F | 6.0% | | |
| CUP-3F.F | 6.0% | | |
| CUP-5F.F | 5.0% | | |
| CUP-3OCCF$_2$.F.F | 9.0% | | |
| CUP-5OCCF$_2$.F.F | 9.0% | | |
| CBC-33F | 3.5% | | |
| CBC-53F | 3.0% | | |
| CBC-55F | 3.0% | | |
| Example XVII | | | |
| PCH-6F | 4.5% | S → N [°C.]: | <−40 |
| PCH-7F | 4.0% | Clearing point [°C.]: | +96 |
| CCP-2OCCF$_2$.F.F | 16.0% | Δn [589 nm, 20° C.]: | +0.108 |
| CCP-3OCCF$_2$.F.F | 15.0% | Δε [1 kHz, 20° C.]: | |
| CCP-5OCCF$_2$.F.F | 16.0% | V$_{(10,0,20)}$ [V]: | 1.23 |
| CUP-2F.F | 6.0% | V$_{(90,0,20)}$ [V]: | 1.95 |
| CUP-3F.F | 6.0% | | |
| CUP-5F.F | 5.0% | | |
| CUP-3OCCF$_2$.F.F | 9.0% | | |
| CUP-5OCCF$_2$.F.F | 9.0% | | |
| CBC-33F | 3.5% | | |
| CBC-53F | 3.0% | | |
| CBC-55F | 3.0% | | |
| Example XVIII | | | |
| PCH-6F | 4.5% | S → N [°C.]: | <−40 |
| PCH-7F | 4.0% | Clearing point [°C.]: | +87 |
| CCP-2OCF$_2$.F.F | 16.0% | Δn [589 nm, 20° C.]: | +0.103 |
| CCP-3OCF$_2$.F.F | 15.0% | Δε [1 kHz, 20° C.]: | |
| CCP-5OCF$_2$.F.F | 16.0% | V$_{(10,0,20)}$ [V]: | 1.15 |
| CUP-2OCH=CF$_2$.F.F | 6.0% | V$_{(90,0,20)}$ [V]: | 1.86 |
| CUP-3OCH=CF$_2$.F.F | 6.0% | | |
| CUP-5OCH=CF$_2$.F.F | 5.0% | | |
| CUP-3OCCF$_2$.F.F | 9.0% | | |
| CUP-5OCCF$_2$.F.F | 9.0% | | |
| CBC-33F | 3.5% | | |
| CBC-53F | 3.0% | | |
| CBC-55F | 3.0% | | |
| Example XIX | | | |
| PCH-6F | 4.5% | S → N [°C.]: | <−40 |
| PCH-7F | 4.0% | Clearing point [°C.]: | 93 |
| CCP-2OCF=CF$_2$.F.F | 16.0% | Δn [589 nm, 20° C.]: | +0.105 |
| CCP-3OCF=CF$_2$.F.F | 15.0% | Δε [1 kHz, 20° C.]: | |
| CCP-5OCF=CF$_2$.F.F | 16.0% | V$_{(10,0,20)}$ [V]: | 1.13 |
| CUP-2F.F | 6.0% | V$_{(90,0,20)}$ [V]: | 1.80 |
| CUP-3F.F | 6.0% | | |
| CUP-5F.F | 5.0% | | |
| CUP-3OCCF$_2$.F.F | 9.0% | | |
| CUP-5OCCF$_2$.F.F | 9.0% | | |
| CBC-33F | 3.5% | | |
| CBC-53F | 3.5% | | |
| CBC-55F | 3.0% | | |
| Example XX | | | |
| PCH-6F | 3.5% | S → N [°C.]: | |
| CCP-2OCF$_2$.F.F | 16.0% | Clearing point [°C.]: | +119 |
| CCP-3OCF$_2$.F.F | 15.0% | Δn [589 nm, 20° C.]: | +0.1158 |
| CCP-5OCF$_2$.F.F | 16.0% | Δε [1 kHz, 20° C.]: | |
| CUP-2F.F | 5.0% | V$_{(10,0,20)}$ [V]: | 1.51 |
| CUP-3F.F | 5.0% | V$_{(90,0,20)}$ [V]: | 2.34 |
| CUP-5F.F | 5.0% | | |
| BCH-3OCCF$_2$.F.F | 10.0% | | |
| BCH-5OCCF$_2$.F.F | 10.0% | | |
| CBC-33F | 5.0% | | |
| CBC-53F | 5.0% | | |
| CBC-55F | 5.0% | | |
| Example XXI | | | |
| PCH-5F | 9.0% | S → N [°C.]: | |
| CCP-2OCF$_2$.F.F | 16.0% | Clearing point [°C.]: | +98 |
| CCP-3OCF$_2$.F.F | 15.0% | Δn [589 nm, 20° C.]: | +0.1082 |
| CCP-5OCF$_2$.F.F | 16.0% | Δε [1 kHz, 20° C.]: | |
| CUP-2F.F | 5.0% | V$_{(10,0,20)}$ [V]: | 1.33 |
| CUP-3F.F | 5.0% | V$_{(90,0,20)}$ [V]: | 2.12 |
| CUP-5F.F | 5.0% | | |
| BCH-3OCCF$_2$.F.F | 10.0% | | |
| BCH-5OCCF$_2$.F.F | 10.0% | | |

-continued
Mixture examples

| | | | |
|---|---|---|---|
| CBC-33F | 3.0% | | |
| CBC-53F | 3.0% | | |
| CBC-55F | 3.0% | | |
| Example XXII | | | |
| PCH-5F | 3.0% | S → N [°C.]: | |
| PCH-7F | 6.0% | Clearing point [°C.]: | +95 |
| CCP-2OCF$_3$ | 11.0% | Δn [589 nm, 20° C.]: | +0.0943 |
| CCP-3OCF$_3$ | 12.0% | Δε [1 kHz, 20° C.]: | |
| CCP-4OCF$_3$ | 10.0% | V$_{(10,0,20)}$ [V]: | 1.55 |
| CCP-5OCF$_3$ | 12.0% | V$_{(90,0,20)}$ [V]: | 2.41 |
| BCH-3XOCCF$_2$.F.F | 12.0% | | |
| BCH-5XOCCF$_2$.F.F | 11.0% | | |
| CCP-3F.F.F | 12.0% | | |
| CCP-5F.F.F | 9.0% | | |
| Example XXIII | | | |
| PCH-5F | 3.0% | S → N [°C.]: | |
| CCP-2OCF$_2$.F.F | 16.0% | Clearing point [°C.]: | +114 |
| CCP-3OCF$_2$.F.F | 15.0% | Δn [589 nm, 20° C.]: | +0.1140 |
| CCP-5OCF$_2$.F.F | 16.0% | Δε [1 kHz, 20° C.]: | |
| CUP-2F.F | 5.0% | V$_{(10,0,20)}$ [V]: | 1.38 |
| CUP-3F.F | 5.0% | V$_{(90,0,20)}$ [V]: | 2.18 |
| CUP-5F.F | 5.0% | | |
| CBC-33F | 5.0% | | |
| CBC-53F | 5.0% | | |
| BCH-3XOCCF$_2$.F.F | 10.0% | | |
| BCH-5XOCCF$_2$.F.F | 10.0% | | |
| Example XXIV | | | |
| PCH-5F | 8.0% | S → N [°C.]: | |
| CCP-2OCF$_2$.F.F | 16.0% | Clearing point [°C.]: | +93 |
| CCP-3OCF$_2$.F.F | 15.0% | Δn [589 nm, 20° C.]: | +0.1057 |
| CCP-5OCF$_2$.F.F | 16.0% | Δε [1 kHz, 20° C.]: | |
| CUP-2F.F | 5.0% | V$_{(10,0,20)}$ [V]: | |
| CUP-3F.F | 5.0% | V$_{(90,0,20)}$ [V]: | |
| CUP-5F.F | 5.0% | | |
| BCH-3XOCCF$_2$.F | 10.0% | | |
| BCH-5XOCCF$_2$.F | 10.0% | | |
| CBC-33F | 4.0% | | |
| CBC-53F | 3.0% | | |
| CBC-55F | 3.0% | | |
| Example XXV | | | |
| PCH-5F | 6.5% | S → N [°C.]: | |
| CCP-2OCF$_2$.F.F | 16.0% | Clearing point [°C.]: | +99 |
| CCP-3OCF$_2$.F.F | 15.0% | Δn [589 nm, 20° C.]: | +0.1078 |
| CCP-5OCF$_2$.F.F | 16.0% | Δε [1 kHz, 20° C.]: | |
| CUP-2F.F | 5.0% | V$_{(10,0,20)}$ [V]: | 1.29 |
| CUP-3F.F | 5.0% | V$_{(90,0,20)}$ [V]: | 2.05 |
| CUP-5F.F | 5.0% | | |
| BCH-3XOCCF$_2$.F | 10.0% | | |
| BCH-5XOCCF$_2$.F | 10.0% | | |
| CBC-33F | 4.5 | | |
| CBC-53F | 4.0% | | |
| CBC-55F | 3.0% | | |
| Example XXVI | | | |
| PCH-5F | 5.0% | S → N [°C.]: | |
| PCH-7F | 6.0% | Clearing point [°C.]: | +88 |
| CCP-2OCF$_3$ | 11.0% | Δn [589 nm, 20° C.]: | +0.0914 |
| CCP-3OCF$_3$ | 12.0% | Δε [1kHz, 20° C.]: | |
| CCP-4OCF$_3$ | 10.0% | V$_{(10,0,20)}$ [V]: | 1.42 |
| CCP-5OCF$_3$ | 12.0% | V$_{(90,0,20)}$ [V]: | 2.26 |
| BCH-3XOCCF$_2$.F.F | 12.0% | | |
| BCH-5XOCCF$_2$.F.F | 11.0% | | |
| CCP-3F.F.F | 12.0% | | |
| CCP-5F.F.F | 9.0% | | |
| Example XXVII | | | |
| PCH-5F | 3.0% | S → N [°C.]: | |
| CCP-2OCF$_2$.F.F | 16.0% | Clearing point [°C.]: | +96 |
| CCP-3OCF$_2$.F.F | 15.0% | Δn [589 nm, 20° C.]: | +0.1061 |
| CCP-5OCF$_2$.F.F | 16.0% | Δε [1 kHz, 20° C.]: | |
| CUP-2F.F | 5.0% | V$_{(10,0,20)}$ [V]: | 1.24 |
| CUP-3F.F | 5.0% | V$_{(90,0,20)}$ [V]: | 1.92 |
| CUP-5F.F | 5.0% | | |
| CUP-3OCCF$_2$.F.F | 10.0% | | |
| CUP-5OCCF$_2$.F.F | 10.0% | | |
| CBC-33F | 4.0% | | |
| CBC-53F | 4.0% | | |
| CBC-55F | 4.0% | | |
| Example XXVIII | | | |
| PCH-5F | 5.0% | S → N [°C.]: | |
| CCP-2OCF$_2$.F.F | 16.0% | Clearing point [°C.]: | +100 |

-continued

| Mixture examples | | | |
|---|---|---|---|
| CCP-3OCF$_2$.F.F | 15.0% | Δn [589 nm, 20° C.]: | +0.1077 |
| CCP-5OCF$_2$.F.F | 16.0% | Δε [1 kHz, 20° C.]: | |
| CUP-2F.F | 5.0% | V$_{(10,0,20)}$ [V]: | 1.25 |
| CUP-3F.F | 5.0% | V$_{(90,0,20)}$ [V]: | 1.97 |
| CUP-5F.F | 5.0% | | |
| CUP-3OCCF$_2$.F.F | 10.0% | | |
| CUP-5OCCF$_2$.F.F | 10.0% | | |
| CBC-33F | 5.0% | | |
| CBC-53F | 4.5% | | |
| CBC-55F | 3.5% | | |

What is claimed is:

1. A liquid-crystalline medium which is essentially free of nitrile-containing compounds comprising a mixture of polar compounds having positive dielectric anisotropy, wherein the polar compounds include one or more compounds of the formula I

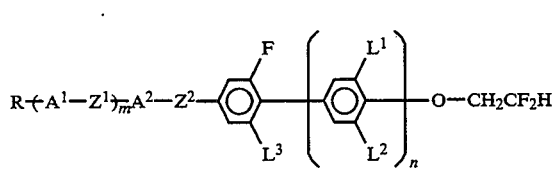

in which
R is H, an alkyl radical of 1 to 15 carbon atoms or alkenyl radical of 2 to 15 carbon atoms which is unsubstituted, monosubstituted by CN or CF$_3$ or mono-to perhalo-substituted by halogen, and, optionally, one or more CH$_2$ groups in these radicals can be replaced, in each case independently of one another, by —O—, —S—,

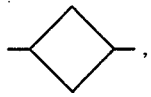

—CO—, —CO—O—, —O—CO— or —O—CO—O, such that O atoms are not linked directly to one another,
A$^1$ and A$^2$ are each, independently of one another, a
 (a) trans-1,4-cyclohexylene radical in which, optionally, one or more non-adjacent CH$_2$ groups can be replaced by —O— and/or —S—,
 (b) 1,4-phenylene radical in which, optionally, one or two CH groups can be replaced by N, or
 (c) radical from the group consisting of 1,4-cyclohexenylene, 1,4-bicyclo(2,2,2)-octylene, piperidine-1,4-diyl, naphthalene-2,6-diyl, decahydronaphthalene-2,6-diyl and 1,2,3,4-tetrahydronaphthalene-2,6-diyl, the radicals (a) and (b) optionally being substituted by one or two fluorine atoms,
Z$^1$ and Z$^2$ are each, independently of one another, —CO—O—, —O—CO—, —CH$_2$O—, —OCH$_2$—, —CH$_2$CH$_2$—, —CH=CH—, —C≡C— or a single bond, and one of the radicals Z$^1$ and Z$^2$, optionally, is alternatively —(CH$_2$)$_4$— or —CH=CH—CH$_2$CH$_2$—,
L$^1$, L$^2$ and L$^3$ are each, independently of one another, H or F,
m is 0, 1 or 2,
n is 0 or 1.

2. The medium according to claim 1 wherein the polar compounds, further include one or more compounds selected from the group consisting of the formulae II, III, IV and V:

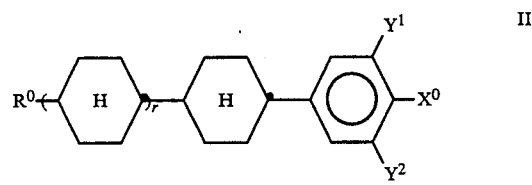

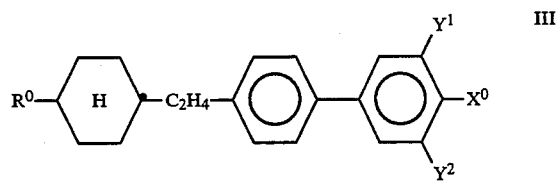

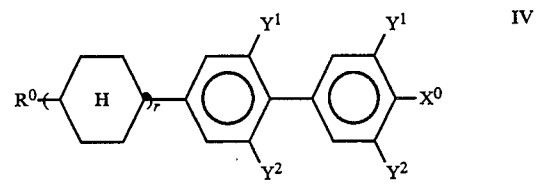

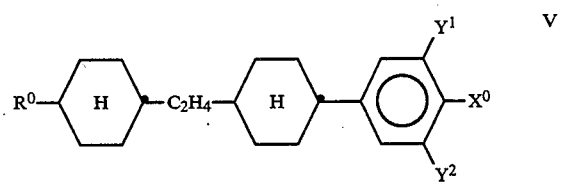

in which the individual radicals are as defined below:
R$^o$ is alkyl, oxaalkyl, fluoroalkyl or alkenyl, in each case having 1 to 7 carbon atoms,
X$^o$ is F, Cl, CF$_3$, OCF$_3$, OCHF$_2$, OCH=CF$_2$, OCF=CF$_2$, OCFH—CF$_2$H or OCF$_2$—CF$_2$H,
Y$^1$ and Y$^2$ are each, independently of one another H or F,
r is 0 or 1.

3. The medium according to claim 2 wherein the polar compounds, further include one or more compounds selected from the group consisting of the formulae VI to XI:

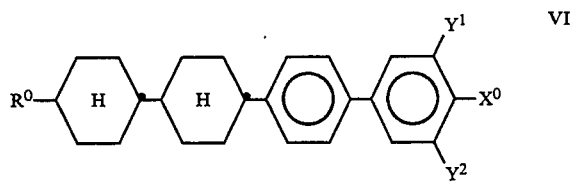

-continued

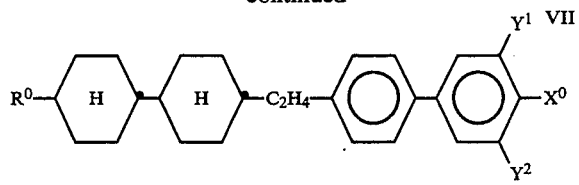

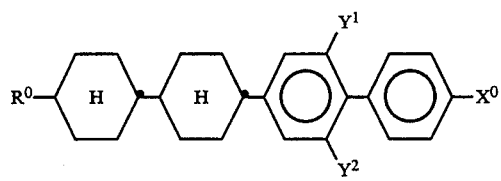

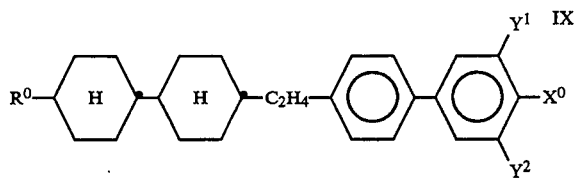

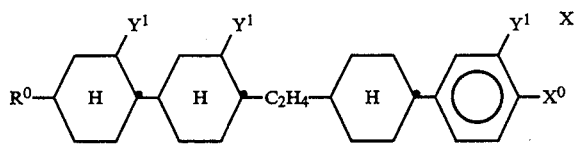

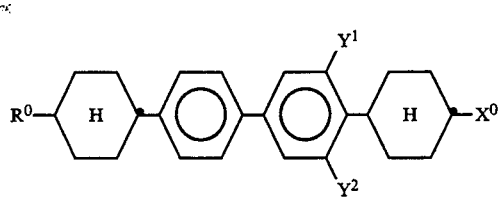

in which $R^0$, $Y^1$ and $Y^2$ each, independently of one another, have a meaning defined in claim 2, and $X^o$ is F, Cl, $F_3$, $OCF_3$, $OCHF_2$, alkyl, oxaalkyl, fluoroalkyl or alkenyl, each having up to 7 carbon atoms.

4. The medium according to claim 2 wherein the polar compounds, further include one or more compounds selected from the group consisting of the formulae VI to XI:

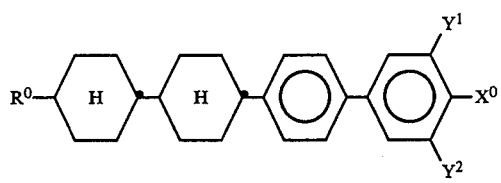

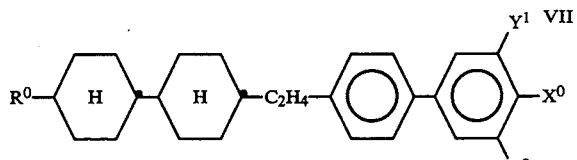

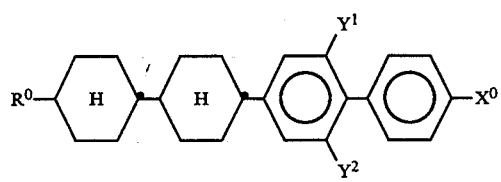

-continued

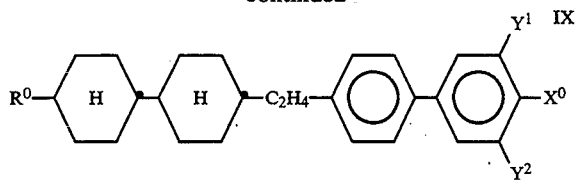

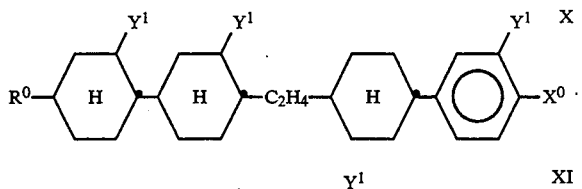

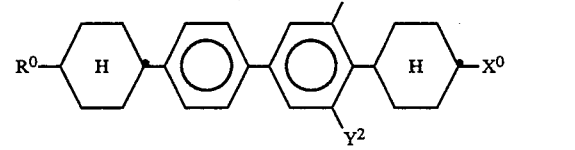

in which $R^o$, $X^o$, $Y^1$ and $Y^2$ each, independently of one another, have a meaning defined below:

$R^o$ is alkyl, oxaalkyl, fluoroalkyl or alkenyl, in each case having 1 to 7 carbon atoms, $X^o$ is F, Cl, $CF_3$, $OCF_3$, $OCHF_2$, $OCH=CF_2$, $OCF=CF_2$, $OCFH-CF_2H$ or $OCF_2-CF_2H$, and $Y^1$ and $Y^2$ are each, independently of one another H or F.

5. The medium of claim 2, wherein the proportion of compounds of the formula I to V together is at least 50% by weight in the total mixture.

6. The medium according to claim 1, wherein the proportion of compounds of the formula I is from 3 to 80% by weight in the total mixture.

7. The medium according to claim 2, wherein the proportion of compounds of the formulae II to V is from 20 to 80% by weight in the total mixture.

8. The medium according to claim 3, which consists essentially of compounds selected from the group consisting of the compounds of the formulae I to XI.

9. The medium according to claim 1, which contains a compound of the formula I13

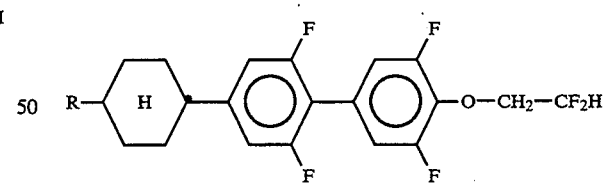

10. An electrooptical liquid-crystal display containing a liquid-crystalline medium according to claim 11. A compound of the formula I

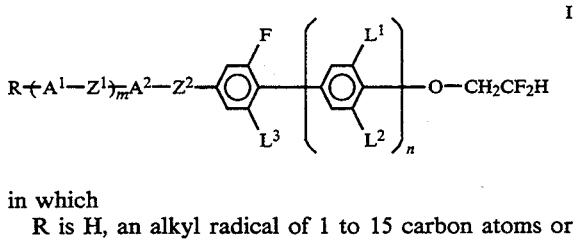

in which

R is H, an alkyl radical of 1 to 15 carbon atoms or alkenyl radical of 2 to 15 carbon atoms which is unsubstituted, monosubstituted by CN or CF₃ or mono-to perhalo-substituted by halogen, and, optionally, one or more CH₂ groups in these radicals can be replaced, in each case independently of one another, by —O—, —S—,

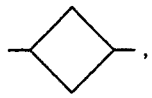

—CO—, —CO—O—, —O—CO— or —O—CO—O, such that 0 atoms are not linked directly to one another, A¹ and A² are each, independently of one another, a
  a) trans-1,4-cyclohexylene radical in which, optionally, one or more non-adjacent CH₂ groups may be replaced by —O— and/or —S—,
  (b) 1,4-phenylene radical in which, optionally, one or two CH groups can be replaced by N, or
  (c) radical from the group consisting of 1,4-cyclohexenylene, 1,4-bicyclo(2,2,2)-octylene, piperidine-1,4-diyl, naphthalene-2,6-diyl, decahydronaphthalene-2,6-diyl and 1,2,3,4-tetrahydronaphthalene-2,6-diyl, the radicals (a) and (b) optionally being substituted by one or two fluorine atoms, Z¹ and Z² are each, independently of one another, —CO—O—, —O—CO—, —CH₂O—, —OCH₂—, —CH₂CH₂—, —CH=CH—, —C≡C— or a single bond, and one of the radicals Z¹ and Z² is, optionally, alternatively —(CH₂)₄— or —CH=CH—CH₂CH₂—, L¹, L² and L³ are each, independently of one another, H or F, m is 0, 1 or 2, n is 1.

12. A compound of claim 11 of the formula

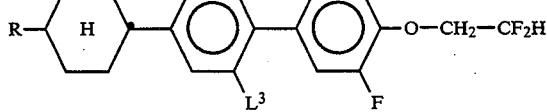

wherein L³ is H or F.

13. A compound of the formula III*,

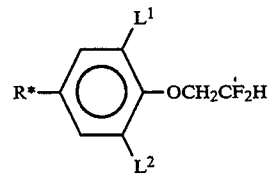

in which
R* is halogen or formyl, and
L¹ and L² are each, independently of one another, H or F.

14. A process for the preparation of a substituted 2,2-difluoroethoxybenzene from the corresponding phenoxide, wherein the phenoxide is reacted with 1-bromo-2,2-difluoroethane in the presence of an inert solvent.

15. The process according to claim 14, wherein the reaction is carried out at temperatures of 20° C. to the boiling point of the inert solvent.

16. The process according to claim 14, wherein the inert solvent is selected from the group consisting of dimethylamide (DMA), hexamethylphosphoric triamide (HMPTA), N-methylpyrrolidone (NMP), N,N-dimethylpropyleneurea (DMPU) and 1,3-dimethyl-2-imidazolidinone (DMEU).

17. The medium of claim 1, which comprises one or more compounds of formula I, wherein n is 1.

18. The medium of claim 17, which comprises one or more compounds of formula I, wherein L³ is F.

19. The medium of claim 17, which comprises one or more compounds of formula I, wherein L¹ and L² are F.

* * * * *

UNITED STATES PATENT AND TRADEMARK OFFICE
CERTIFICATE OF CORRECTION

PATENT NO. : 5,422,035
DATED : June 6, 1995
INVENTOR(S) : BARTMANN et al.

It is certified that error appears in the above-indentified patent and that said Letters Patent is hereby corrected as shown below:

Claim 10; column 70, line 56: After claim insert

-- 1. --.

Signed and Sealed this

Twenty-sixth Day of September, 1995

Attest:

BRUCE LEHMAN

*Attesting Officer*     *Commissioner of Patents and Trademarks*